US010451584B2

(12) United States Patent
Yanagawa et al.

(10) Patent No.: US 10,451,584 B2
(45) Date of Patent: Oct. 22, 2019

(54) BIOMOLECULE MEASURING DEVICE

(71) Applicant: HITACHI HIGH-TECHNOLOGIES CORPORATION, Tokyo (JP)

(72) Inventors: Yoshimitsu Yanagawa, Tokyo (JP); Takahide Yokoi, Tokyo (JP); Naoshi Itabashi, Tokyo (JP); Takayuki Kawahara, Tokyo (JP); Sonoko Migitaka, Tokyo (JP); Makiko Yoshida, Tokyo (JP); Takamichi Muramatsu, Tokyo (JP)

(73) Assignee: Hitachi High-Technologies Corporation, Tokyo (JP)

(*) Notice: Subject to any disclaimer, the term of this patent is extended or adjusted under 35 U.S.C. 154(b) by 214 days.

(21) Appl. No.: 14/759,596

(22) PCT Filed: Nov. 18, 2013

(86) PCT No.: PCT/JP2013/081014
§ 371 (c)(1),
(2) Date: Jul. 7, 2015

(87) PCT Pub. No.: WO2014/112199
PCT Pub. Date: Jul. 24, 2014

(65) Prior Publication Data
US 2015/0362458 A1 Dec. 17, 2015

(30) Foreign Application Priority Data

Jan. 17, 2013 (JP) .................................. 2013-006391

(51) Int. Cl.
*G01N 27/414* (2006.01)
(52) U.S. Cl.
CPC ................................ *G01N 27/4145* (2013.01)

(58) Field of Classification Search
CPC ............ G01N 27/4145; B01J 19/0046; C12Q 1/6874; C12Q 1/6825; G06F 19/22
See application file for complete search history.

(56) References Cited

U.S. PATENT DOCUMENTS 5,466,348 A * 11/1995 Holm-Kennedy ..........................
G01N 33/54373
204/403.01
2005/0170347 A1 * 8/2005 Miyahara ............. B01J 19/0046
506/9

(Continued)

FOREIGN PATENT DOCUMENTS

CN 102124128 A 7/2011
CN 102301228 A 12/2011

(Continued)

OTHER PUBLICATIONS

P. Georgiou et al., ISFET threshold voltage programming in CMOS using hot-electron injection, Electronics Letter, Oct. 22, 2009, vol. 45, No. 22.

(Continued)

*Primary Examiner* — Maris R Kessel
*Assistant Examiner* — Joshua L Allen
(74) *Attorney, Agent, or Firm* — Mattingly & Malur, PC

(57) ABSTRACT

Provided is a biomolecule measuring device capable of effectively reducing measurement noise occurring when measuring a biomolecule sample using a semiconductor sensor. This biomolecule measuring device generates a trigger to react a sample with a reagent after starting to send the reagent onto the semiconductor sensor that detects ion concentration (see FIG. 7).

14 Claims, 21 Drawing Sheets

(56) References Cited

U.S. PATENT DOCUMENTS

| | | | |
|---|---|---|---|
| 2010/0137143 A1* | 6/2010 | Rothberg | C12Q 1/6874 506/2 |
| 2010/0197001 A1* | 8/2010 | Miyahara | C12Q 1/6825 435/287.2 |
| 2010/0282617 A1* | 11/2010 | Rothberg | C12Q 1/6825 205/780.5 |
| 2011/0065101 A1* | 3/2011 | Bell | B01L 3/502753 435/6.19 |
| 2011/0230375 A1* | 9/2011 | Rothberg | C12Q 1/6869 506/39 |
| 2012/0172241 A1 | 7/2012 | Rearick et al. | |
| 2012/0173159 A1* | 7/2012 | Davey | G06F 19/22 702/20 |

FOREIGN PATENT DOCUMENTS

| | | |
|---|---|---|
| EP | 1 460 130 A1 | 9/2004 |
| JP | 2010-513869 A | 4/2010 |
| JP | 2010-519914 A | 6/2010 |
| JP | 2012-506557 A | 3/2012 |
| JP | 2012-528329 A | 11/2012 |
| WO | 03/073088 A2 | 9/2003 |
| WO | 2008/076406 A2 | 6/2008 |
| WO | 2008/107014 A1 | 9/2008 |
| WO | 2009/006445 A1 | 1/2009 |
| WO | 2009-155181 A1 | 12/2009 |
| WO | 2010/047804 A1 | 4/2010 |
| WO | 2010/138182 A2 | 12/2010 |
| WO | 2012/027391 A1 | 3/2012 |

OTHER PUBLICATIONS

Yan Liu et al., An Extended CMOS ISFET Model Incorporating the Physical Design Geometry and the Effects on Performance and Offset Variation, IEEE Transactions on electron Devices, Dec. 2011, pp. 4414-4422, vol. 58, No. 12.

Paul A. Hammond et al., Design of a Single-Chip pH Sensor Using a Conventional 0.6-um CMOS Process, IEEE Sensors Journal, Dec. 2004, pp. 706-712, vol. 4, No. 6.

Mark J. Milgrew et al., Matching the Transconductance Characteristics CMOS ISFET Arrays by Removing Trapped Charge, IEEE Transactions on Electron Devices, Apr. 2008, pp. 1074-1079.

J.C. van Kerhof et al., ISFET responses on a stepwise change in electrolyte concentration at constant pH, Sensor and Actuators B, 18-19 (1994), pp. 56-59.

International Search Report of PCT/JP2013/081014.

Extended European Search Report received in corresponding European Application No. 13871321.9 dated Jul. 25, 2016.

Chinese Office Action received in corresponding Chinese Application No. 201380069342.2 dated May 17, 2016.

* cited by examiner

FIG. 1
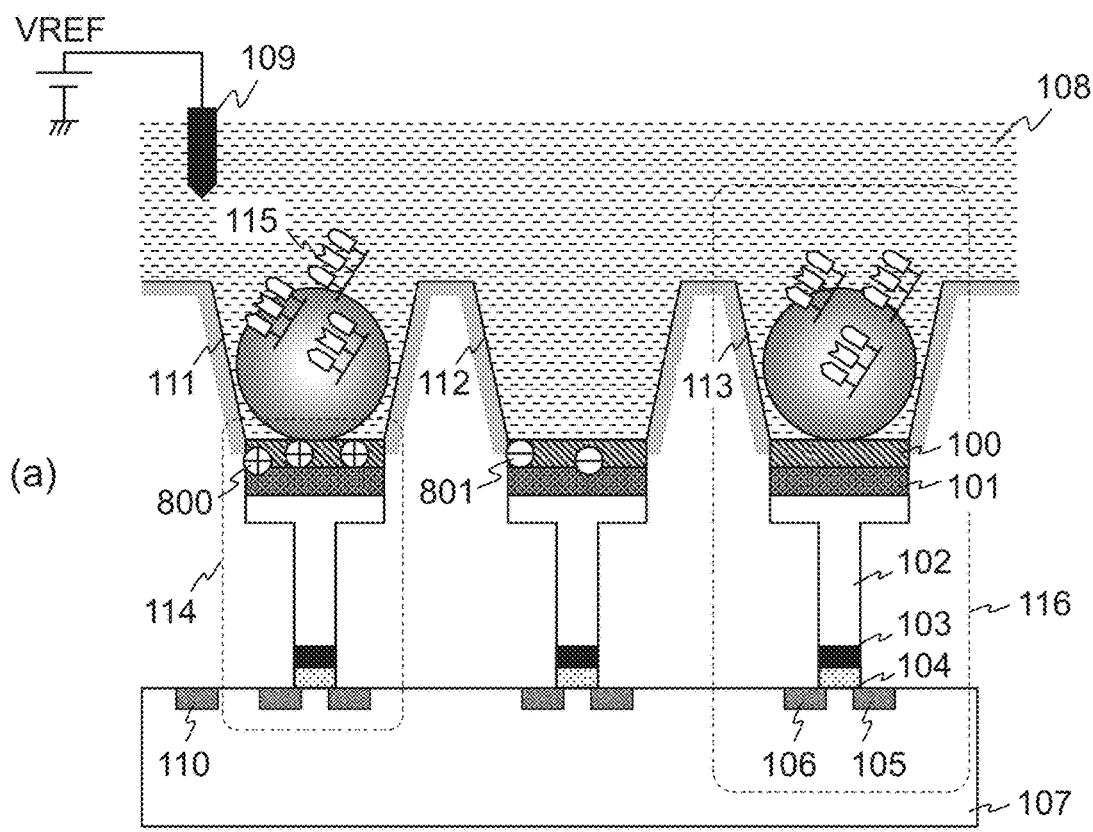
(a)
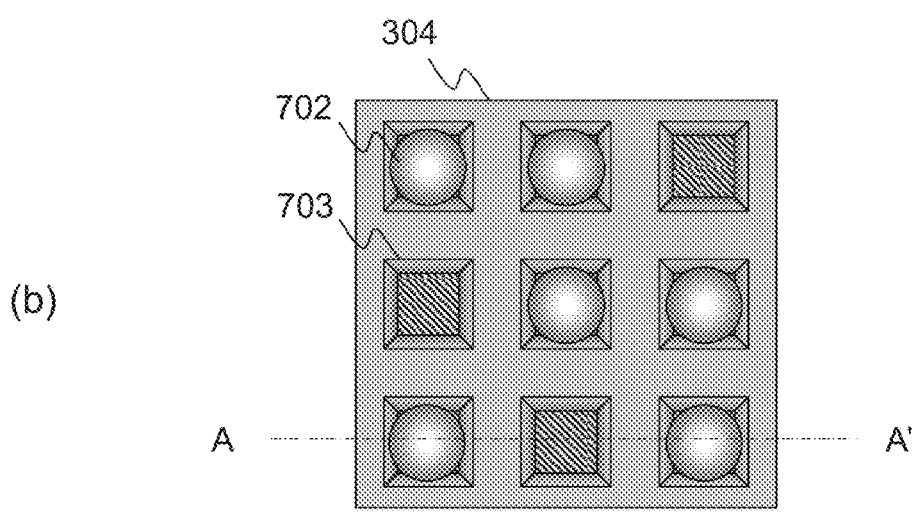
(b)

FIG. 13
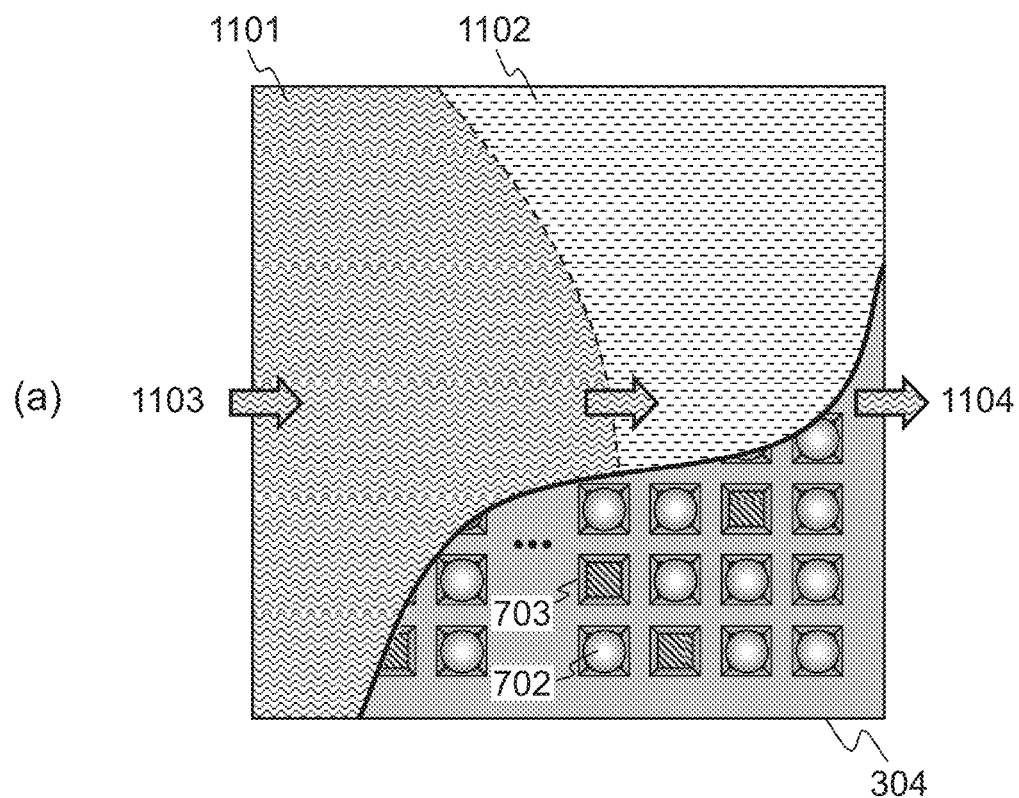
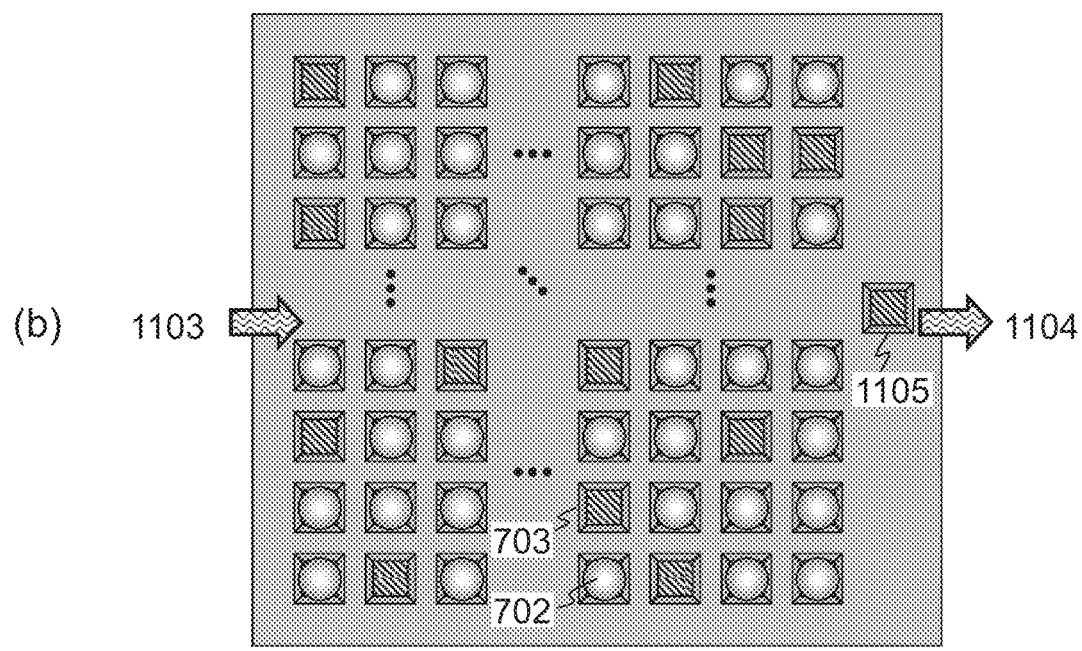

BIOMOLECULE MEASURING DEVICE

TECHNICAL FIELD

The present invention relates to a biomolecule measuring device.

BACKGROUND ART

In recent years, biomolecule measuring devices using semiconductor technologies are drawing attentions. Patent Literature 1 listed below describes a DNA sequencer that cost-effectively and rapidly determines base sequences of deoxyribo nucleic acid (DNA) using pH sensor arrays manufactured with semiconductor technologies. Semiconductor sensors quantify reactions of target biomaterials according to magnitude of electrical signals. Therefore, semiconductor sensors do not require conventional expensive fluorescent reagents and thus are advantageous in terms of costs. It is possible to integrate millions to more than a billion sensors using semiconductor micro-processing technologies. It is also possible to activate each of such sensors in parallel to perform measurements. Therefore, the throughput of the measurement may be readily improved.

Ion Sensitive Field Effect Transistor (ISFET) is one of semiconductor sensors that is frequently used in the field of biomolecule measuring device. Details of ISFET will be described later. ISFET is a device that measures interface potentials induced on ion sensitive layers. Therefore, if there exists electric charges other than those derived from ions to be measured, measuring errors may be caused by such electric charges. However, plasma processing or ion injection are performed during manufacturing the device in semiconductor processes, thus it is likely that electric charges are accumulated in the device. Regarding that technical problem, Non Patent Literature 1 listed below describes that electric charges are accumulated especially at ion sensitive layers, protection layers, interfaces of electrodes, floating electrodes, or gate oxides. Non Patent Literature 2 listed below describes that such accumulation of electric charges may offset threshold voltages of ISFET by around ±10V.

It is known that ISFET has a technical problem referred to as drift in which characteristics shift during measurement process. Drift is a phenomenon caused by chemical reactions between ion sensitive layers and reagents during measurement process which causes the ion sensitive layer to trap electric charges. The amount of drift significantly depends on manufacturing process of the device or device structures. Non Patent Literature 3 listed below describes that the threshold voltage of transistor shifts at a rate of approximately 10 mV/hour.

The offset or drift of threshold voltage due to trapped charges may cause measuring errors and thus it is necessary to reduce them. Patent Literature 1 listed below describes, as a conventional technique for removing trapped charges, a method to irradiate ultraviolet ray to provide electric charge with energy, thereby withdrawing the charge from the device. Non Patent Literature 4 listed below describes that it is necessary to irradiate ultraviolet ray for long hours, e.g. for 10 hours. Non Patent Literature 1 describes that hot electron injection may reduce variations in threshold voltages due to trapped charges.

Another technical problem in utilizing ISFET for measuring biomolecules is that ISFET also outputs signals in response to variation in ion concentration when replacing reagent solutions. In other words, a signal due to replacing reagent solutions (i.e. background signal) is overlapped with the signal due to variation in ion concentration to be measured. For example, ISFET using $Ta_2O_5$ as ion sensitive layer is excellent in hydrogen ion selectivity and sensitivity, and is widely used as the pH sensor array in Patent Literature 1 and the like. However, Non Patent Literature 5 describes that such ISFET also outputs signals in response to potassium chloride ion in the solution.

In order to acquire only the target signal from the signal overlapped with background signals, it is necessary to estimate the background signal and to subtract the estimated background signal from the acquired signal. Patent Literature 2 listed below describes a method for estimating background signals using calculated signal value of ISFET in a reaction well not including biomolecules. When performing parallel measurement using one million to more than one million ISFETs as in the above-described semiconductor DNA sequencer, it is necessary to perform the above-described background processing for all of measured data in all reaction wells. Then the background processing increases the analyzing time. This indicates that the time until the measurement result is acquired is elongated. Therefore, the background processing time should be reduced as far as possible.

CITATION LIST

Patent Literature

Patent Literature 1: JP Patent Publication (Kohyo) 2010-513869 A

Patent Literature 2: US Patent Publication 2012/0172241

Non Patent Literature

Non Patent Literature 1: Georgiou, et. al, Electronics Lett. October 2009

Non Patent Literature 2: Liu, et. al, IEEE Trans. Elec. Dev, December, 2011

Non Patent Literature 3: Hammond, et. al, IEEE Sensors, December 2004

Non Patent Literature 4: Milgrew, et. Al, IEEE Elec. Dev., April 2008

Non Patent Literature 5: Kerkhof, et. al, Sensors and Actuators B, 1994

SUMMARY OF INVENTION

Technical Problem

The methods for removing trapped charges by irradiating ultraviolet rays described in Patent Literature 1 and Non Patent Literature 4 require irradiating the ultraviolet ray for long time, as mentioned above. This causes a technical problem of increased measuring time. Regarding method for reducing influences from trapped charges, Non Patent Literature 1 discusses about injecting hot electrons to a single ISFET. However, no method is discussed preferable for biomolecule measuring devices in which a plurality of ISFETs is arranged in arrayed manner. In addition, hot electron injection only works for increasing the threshold voltage.

It is conceivable that calibrating the characteristics of the device may be used as another solution. For example, in case of a pH sensor using a single ISFET, a calibration may be done using a standard solution as a pH reference, and then a correction may be applied outside the sensor, thereby keeping the measurement accuracy. However, in case of semiconductor sensor array in which a lot of ISFETs is allocated in arrayed manner, it is necessary to calibrate for each data from vast amount of ISFETs, which is impractical.

On the other hand, in the method regarding background processing described in Patent Literature 2, it is necessary to perform huge amount of calculations for estimating backgrounds and for calculating differences. Thus a lot of time is required from the beginning of measurement until acquiring the result. In addition, when estimating backgrounds using such as averaging calculations, the measurement accuracy for each ISFET may be decreased. Further, in order to precisely estimate backgrounds across wide value range, huge amount of data is required.

The present invention is made in the light of the above-mentioned technical problem. It is an objective of the present invention to provide a biomolecule measuring device that is capable of effectively reducing measurement noises occurring when measuring biomolecule samples using semiconductor sensors.

Solution to Problem

A biomolecule measuring device according to the present invention generates, after starting transmission of a reagent onto a semiconductor sensor that detects an ion concentration, a trigger to react the reagent with a sample.

Advantageous Effects of Invention

With the biomolecule measuring device according to the present invention, it is possible to effectively reduce measurement noises occurring when measuring biomolecule samples using semiconductor sensors that detect ion concentrations.

Technical problems, configurations, and advantageous effects other than those mentioned above will be apparent from the detailed descriptions of embodiments below.

BRIEF DESCRIPTION OF DRAWINGS

FIG. 1 is a diagram showing a configuration of an ISFET array 304.

FIG. 13 is a diagram showing a configuration example in a case where background is removed using some of the ISFETs 114 on the ISFET array chip 1002.

DESCRIPTION OF EMBODIMENTS

Hereinafter, for the sake of promoting understanding of the present invention, a technical problem due to drift, offset, and background in conventional biomolecule measuring devices will be described first. Then embodiments of the present invention will be described.

<Technical Problem in Conventional Techniques: Regarding Measurement Error>

FIG. 1 is a diagram showing a configuration of an ISFET array 304 described later. FIG. 1(a) is a side sectional diagram of three ISFETs 114 and reaction wells (hereinafter, referred to as well) 111-113 included in the ISFET array 304. FIG. 1(a) corresponds to A-A' line sectional view in FIG. 1(b). FIG. 1(b) is a top view of the ISFET array 304. Wires to each transistor are omitted in the figure.

Figure 2:
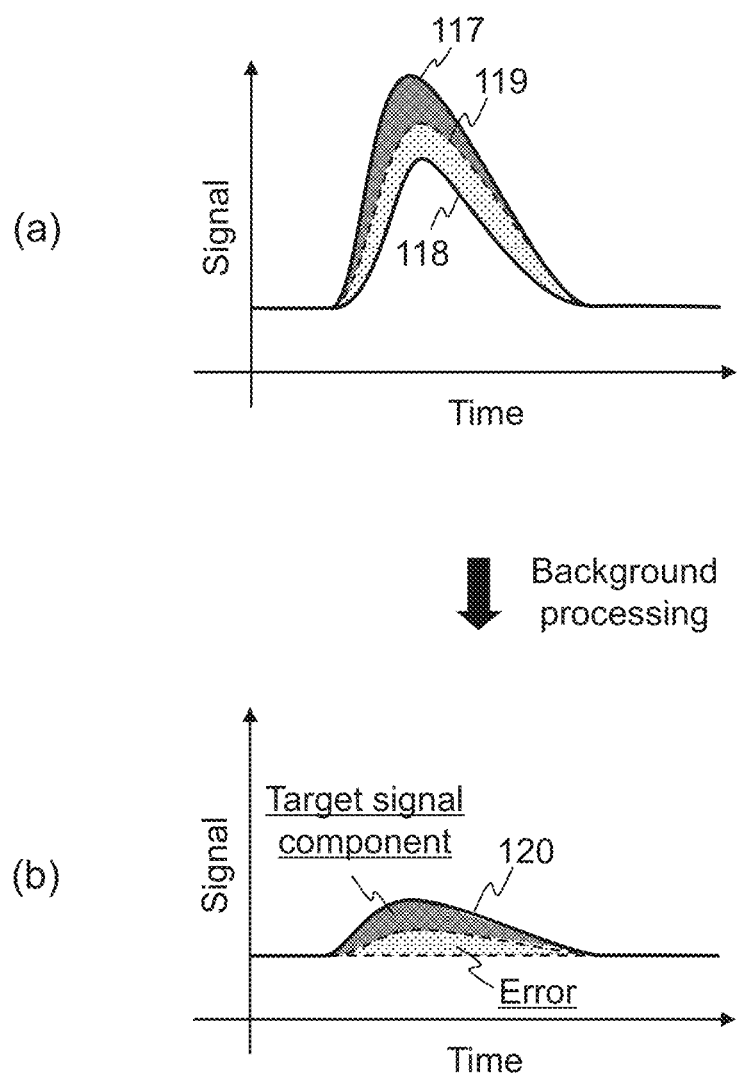
FIG. 2 is a signal waveform diagram showing an example of background processing.

FIG. 2 is a signal waveform diagram showing an example of background processing. As shown in FIG. 2 (a)(b), it is possible to calculate the background signal by subtracting a waveform 118 measured by the empty well 112 from a waveform 117 measured by the well 111. This is because the empty well 112 does not include the DNA 115 to be measured and thus only the background signal is measured caused by injecting the reagent solution 108. However, since the ISFET 114 has variations in characteristics, the background waveform 119 of the well 111 does not strictly matches with the waveform 118 acquired at the empty well 112. Accordingly, the signal waveform 120 acquired by the aforementioned background processing includes an error added to the target signal component.

In order to reduce influences from variations in characteristics of the ISFET 114, Patent Literature 2 estimates the background signal by averaging the measured waveform acquired from a plurality of the empty wells 112 around the well 111. However, the well 111 itself also has variations in characteristics. Therefore, even if the measured waveform acquired from a plurality of the empty wells 112 is averaged, there still remains an error due to each of the wells 111. In addition, the processing load for estimation will be increased.

<Technical Problem in Conventional Techniques: Regarding Data Amount>

As shown in FIG. 1, when manufacturing the chip, a positive charge 800 or a negative charge 801 are trapped on the structure of the ISFET 114. The amount of such charges is different for each of the ISFETs 114. This causes the offset of transistor threshold voltages in the ISFETs 114. The location at which the charges are trapped are mainly: surfaces of the ion sensitive layer 100; interfaces between the ion sensitive layer 100 and the protection layer 101; the floating gate 102; and the gate oxide 104. The transistor threshold voltages of each of the ISFETs 114 offset depending on types and amounts of the trapped charges.

Figure 3:
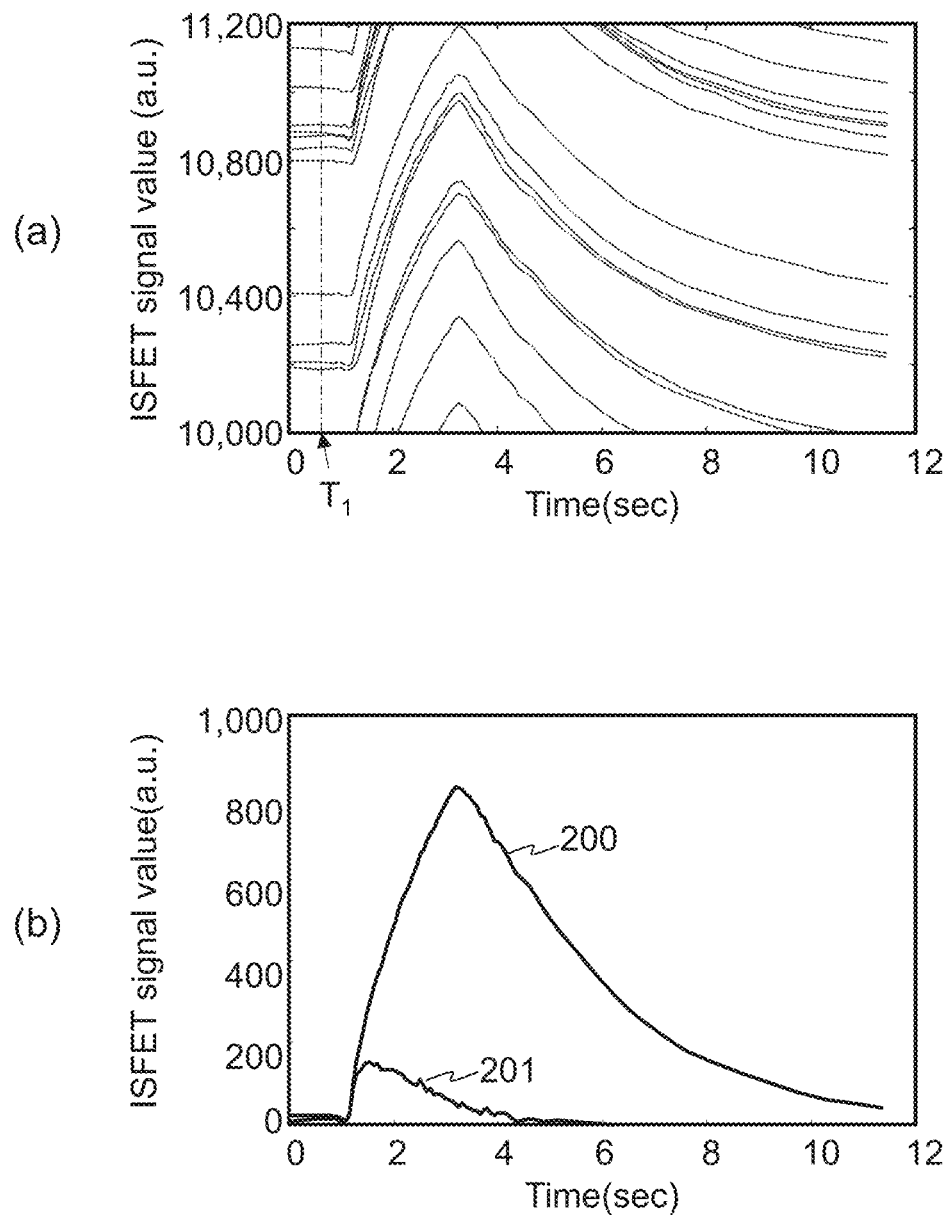
FIG. 3 is a diagram showing an example of waveform of measured signal acquired from an ISFET 114.

FIG. 3 is a diagram showing an example of waveform of measured signal acquired from the ISFET 114. FIG. 3(*a*) shows overlapped signal waveforms of each of the ISFETs 114 acquired by a DNA sequencer including a plurality of the ISFETs 114. As shown in FIG. 3(*a*), there are offsets between the signal waveforms acquired from each of the ISFETs 114. FIG. 3(*b*) shows, for one of these waveforms, a waveform 200 from which the offset is removed and a signal waveform 201 finally acquired by the above-mentioned background processing.

In order to remove the offset and the background from the waveform actually outputted from ISFET using computational process to finally acquire the signal waveform 201, it is necessary to record wide range of waveforms as shown in FIG. 3(*a*) with sufficient resolution. Therefore, the A/D converter that reads out the waveforms requires wide dynamic range. In addition, the outputted data amount will be huge.

For example, a theoretical voltage variation due to variation in hydrogen ion concentration may be calculated using Nernst equation. It is approximately 59 mV/pH at 25 degrees centigrade. Actual ISFET has a slightly lower value, i.e. tens of mV per pH. When measuring this voltage variation with precision of 1 mV, 14 to 15 bits of A/D conversion precision is required for recording all of waveform data offsetting by ±10V. Waveform variation due to pH variation ranges across several seconds. Therefore, when measuring at sampling rate of 100 Hz for 5 seconds, one unit of the ISFET 114 outputs approximately 1 Kbytes of data at each measurement. Assuming that the measurement is repeated 100 times and there are one million wells, the finally outputted data reaches 100 Gbytes. Thus huge amount of data must be stored for saving a plurality of measurement data. On the other hand, assuming that a signal derived from incorporation event varies between pH1-pH14, the voltage variation is 59 mV×14=826 mV, i.e. merely about 1V. Accordingly, even when measuring with precision of 1 mV, the A/D converter only requires 10 bits. Thus the amount of data will be reduced by approximately 30%.

As discussed above, considering the data amount, it is preferable to previously reduce drift, offset, and background of ISFET on the device before data processing. Alternatively, it is preferable if they can be removed only by simple calculations.

<Embodiment 1>

Hereinafter, embodiments of the present invention will be described using figures. An example will be described where ISFET is used as the semiconductor sensor and where the biomolecule measuring device is configured as a DNA sequencer that determines DNA sequences. However, application of the present invention is not limited to DNA sequencers. The present invention may be widely applied to systems that electrically measure reactive products of biomolecules. Since ISFET can detect various types of ions by appropriately selecting the ion sensitive layer, the present invention may be applied to devices that measure biomolecules in which sodium ions or potassium ions vary, for example. In all figures describing the embodiments, same reference signs are basically assigned to same components, and repetitive explanations will be omitted.

Now returning back to FIG. 1. The ISFET array 304 has a plurality of the well 703 arranged two dimensionally. An ion sensitive layer 100 of the ISFET 114 is disposed at the bottom of each of the wells 703. The well 703 is a hole formed by semiconductor process and has a side with size of approximately hundreds of nm to several μm. When measuring, a bead 702 is filled in each of the wells 703. A biomolecule 115 to be measured is attached to the bead 702. If the biomolecule 115 is DNA, the DNA to be measured may be replicated by methods such as emulsion PCR, thereby increasing number of DNA on the bead 702. It increases amount of generated hydrogen ion (details will be described later in FIG. 6), thereby facilitating detection.

The ISFET 114 generally includes the ion sensitive layer 100, the protection layer 101, the floating gate 102, a gate electrode 103, the gate oxide 104, a drain 105, a source 106, a Si substrate 107, and a substrate contact 110. Some configurations do not include the floating gate 102 and the gate electrode 103, and the protection layer 101 and the ion sensitive layer 100 are stacked directly on the gate oxide 104. The ISFET 114 and the well 703 formed immediately above the ISFET 114 may be collectively referred to as a cell 116.

When measuring ions generated from the biomolecule 115, the sensitive layer 100 is contacted with the reagent solution 108 and the reference electrode 109 is immersed into the reagent solution 108. By applying a voltage VREF to the reference electrode 109 under this situation, a channel is induced between the drain 105 and the source 106 via capacitive coupling between the ion sensitive layer 100, the protection layer 101, and the gate oxide 104. Thus a drain current-reference electrode voltage characteristic is acquired depending on the characteristic of the ISFET 114.

Figure 4:
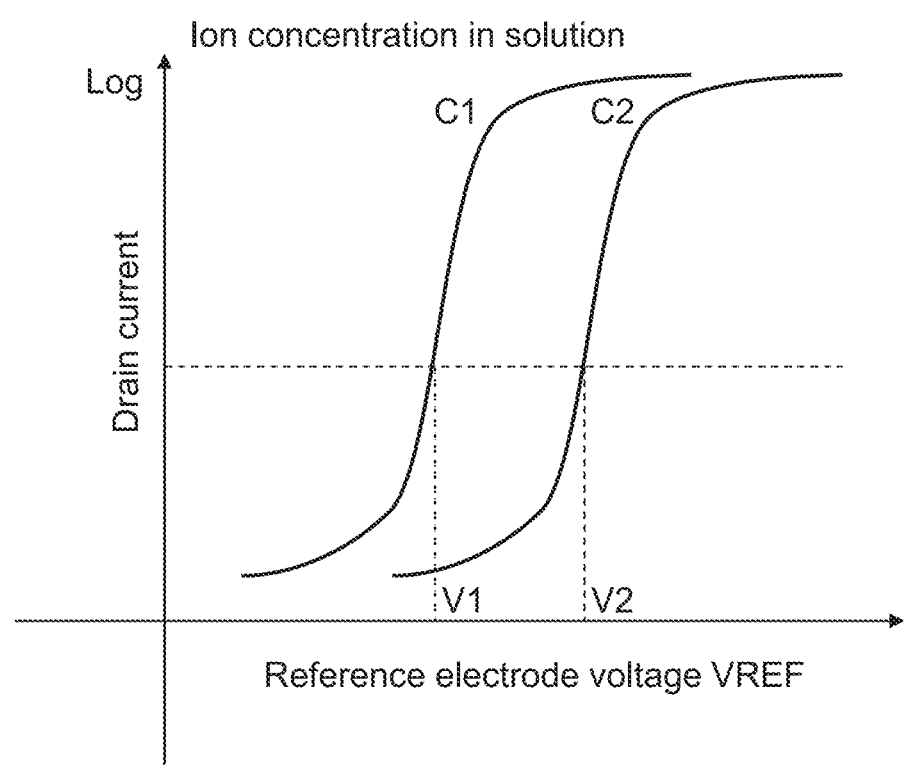
FIG. 4 is a diagram showing an example of drain current-reference electrode voltage characteristic.

FIG. 4 is a diagram showing an example of drain current-reference electrode voltage characteristic. If ions exist in the solution 108, an interface voltage is generated between the ion sensitive layer 100 and the reagent solution 108, and the effective voltage applied to the gate oxide 103 is varied. The magnitude of the interface voltage depends on the ion concentration. For example, when the ion concentration in the solution 108 changes from C1 to C2, the transistor threshold voltage of the ISFET 114 seems varied from V1 to V2. It is possible to measure the ion concentration in the solution 108 from the change in the threshold voltage.

Figure 5:
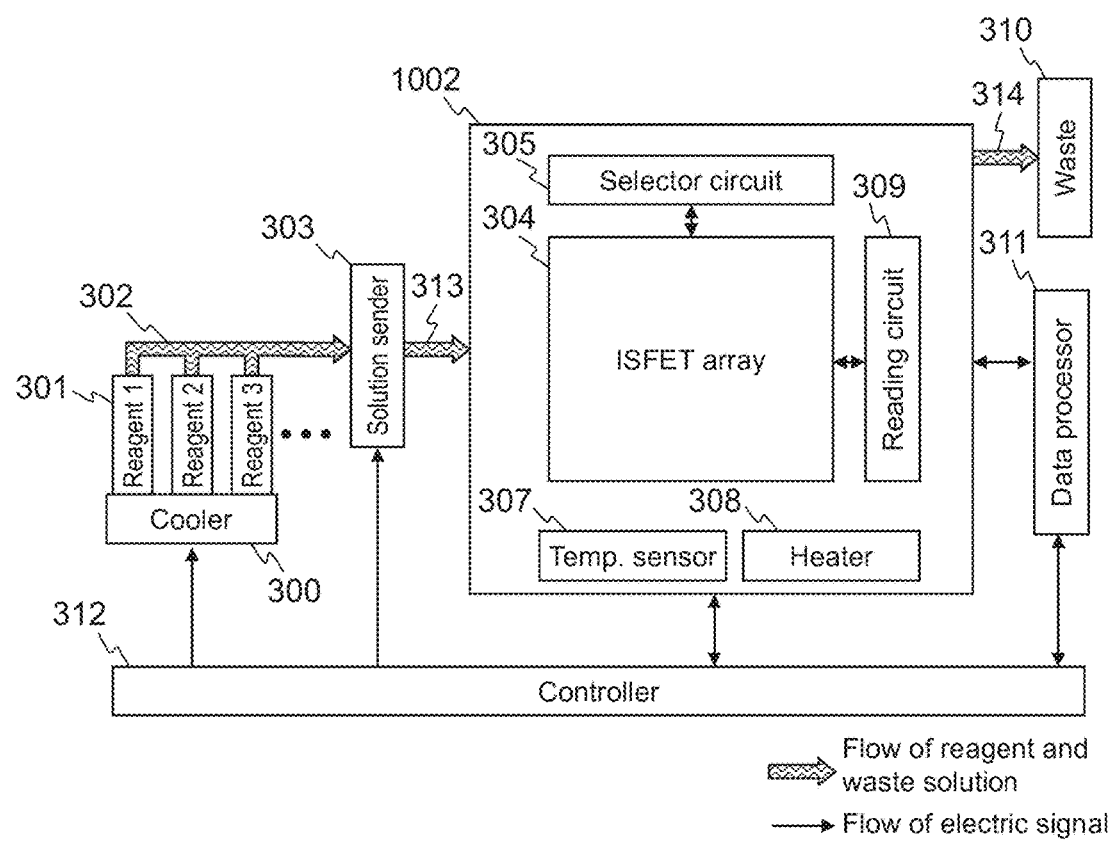
FIG. 5 is a functional block diagram of a biomolecule measuring device according to an embodiment 1.

FIG. 5 is a functional block diagram of a biomolecule measuring device according to the embodiment 1. The biomolecule 115 to be measured is attached to the bead 702 and is filled on the ISFET array 304. A solution sender 303 transmits, from a reagent container 301, the reagent necessary for the biomolecule 115 to react with ions. The reagent reacts with the biomolecule 115 on an ISFET array chip 1002. The ISFET array chip 1002 detects variations in ion concentrations generated by this reaction. The waste solution after the reaction is collected by a waste container 310.

The solution sender 303 may be implemented by using a plurality of typical solution sending pumps, for example. Alternatively, the solution sender 303 may be implemented by: injecting inert gases such as nitrogen or argon into the reagent containers 301 using valves for each of the reagent containers 301 while adjusting the pressure; and pushing out the reagent from the reagent container 301 by the gas pressure.

The controller 312 performs, according to preprogrammed experiment sequences and to the data acquired by the data processor 311, processes of: adjusting the timing for transmitting solutions by the solution sending pumps of the solution sender 303 and adjusting the amount of transmitted solutions; controlling operational states of the ISFET array chip 1002; controlling the data processor 311; controlling voltages of the reference electrodes installed on any one of the reagent routes 302, 313, and 314 or installed on the ISFET chip 1002. The controller 312 also controls, according to the measured value by the temperature sensor 307 installed on the ISFET array chip 1002, the cooler 300 that cools the reagent solution and the heater 308 installed on the ISFET array chip 1002.

The data processor 311 acquires data indicating the measured result outputted from the ISFET array chip 1002 and analyzes the acquired data. The data processor 311 may be implemented by an interface board equipped with typical A/D converters and by a computer. The selector circuit 305 and the reading circuit 309 will be described later.

Figure 6:
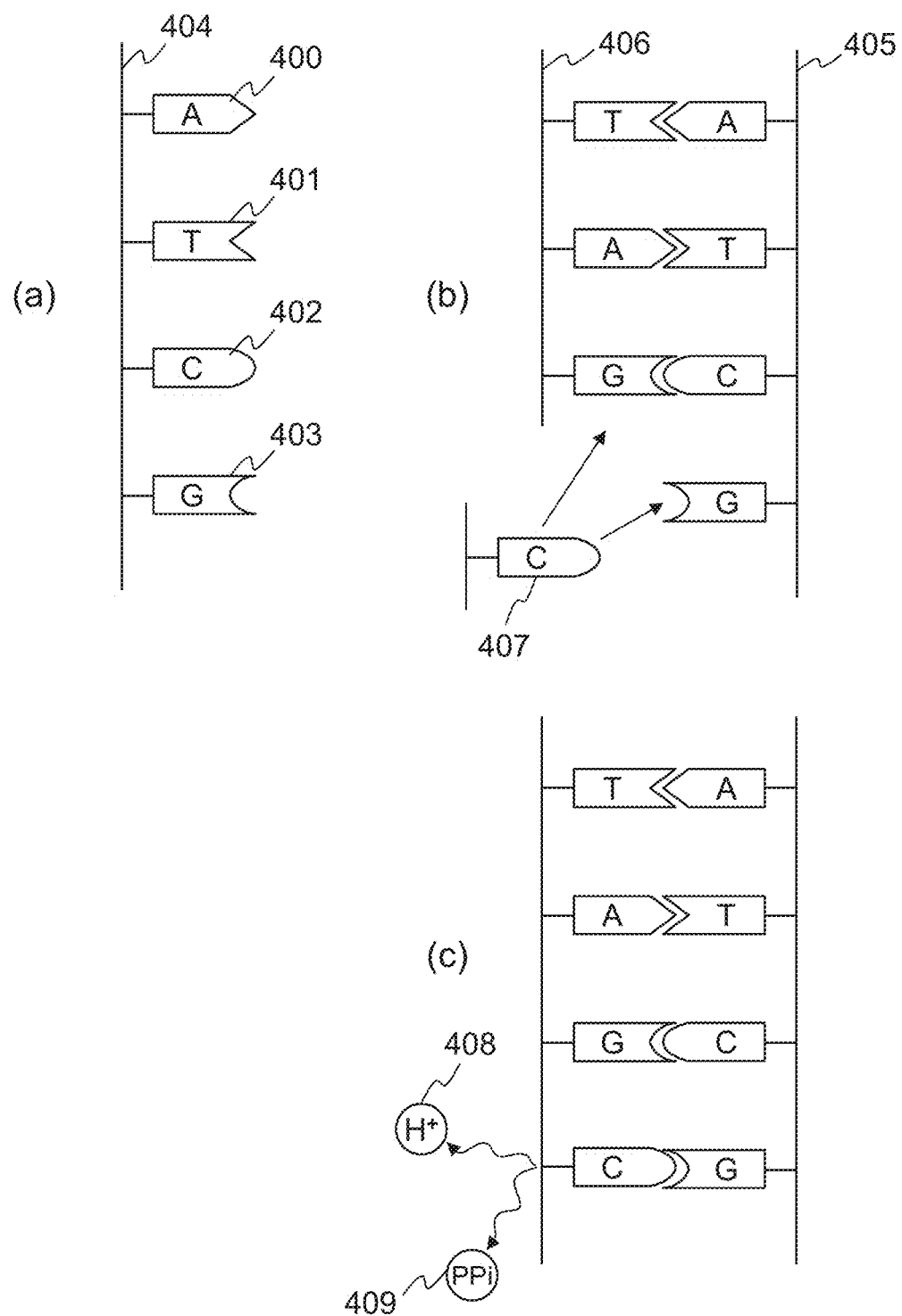
FIG. 6 is a diagram explaining a DNA structure and an incorporation.

FIG. 6 is a diagram explaining a DNA structure and an incorporating event. FIG. 6(a) is a diagram schematically showing single-stranded DNA. In actual single-stranded DNA, four types of bases are coupled with a chain consisted of phosphoric acid and of deoxyribose, thereby forming a complex cubic structure. For the sake of simplicity, the chain consisted of phosphoric acid and of deoxyribose is shown by the straight line 404, and the four types of bases are shown by reference signs of A (400) as adenine, T (401) as thymine, C (402) as cytosine, and G (403) as guanine.

FIG. 6(b) is a diagram schematically showing an incorporation event of DNA. The figure shows a state where a primer 406 consisted of TAG is coupled with the single-strand 405 of ATCG. In this state, if there exists a type (dCTP) 407 of deoxyribonucleotide triphosphate (dNTP) including cytosine and if there exists a DNA polymerase as an incorporating enzyme (not shown in the figure), dCTP is coupled with the end of G, and as shown in FIG. 6(c) a diphosphate 409 and a hydrogen ion 408 are released.

A method for determining the DNA sequence by detecting the hydrogen ion 408 may be defined as below. Firstly, the primer 406 is coupled with the unknown single-stranded DNA 405 which DNA sequence is to be determined. In this state, four types of reagents of dCTP, dTTP, dATP, and dGTP are sequentially injected. The hydrogen ion concentration is measured at each of the reagent injections. For example, if the hydrogen ion is generated when injecting dATP, the end portion of the single-stranded DNA excluding the portion coupled with the primer 406 is a complementary base of A, i.e. T. It is possible to sequentially determine the DNA sequence by repeating the process of reagent injection and of measuring hydrogen ion concentration.

Figure 7:
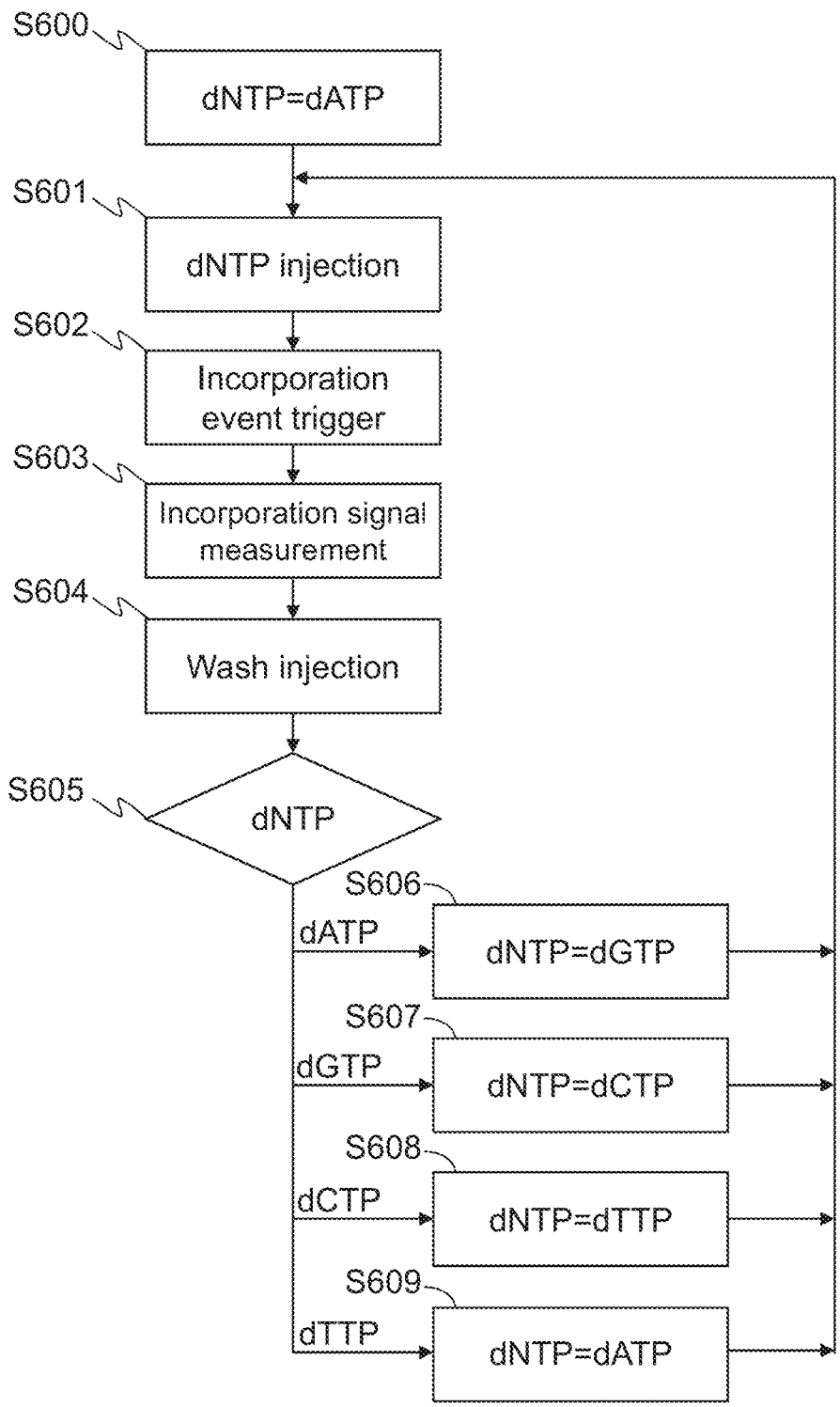
FIG. 7 is a flowchart of a process in which the biomolecule measuring device according to the embodiment 1 determines DNA sequences.

FIG. 7 is a flowchart of a process in which the biomolecule measuring device according to the embodiment 1 determines DNA sequences. Hereinafter, each step in FIG. 7 will be described.

(FIG. 7: Steps S600-S601)

The bead 702 is filled into the cell, and then the ISFET array chip 1002 is mounted on the device. The reagent dNTPs and the wash used for the reaction are previously cooled well below the optimum temperature of DNA polymerase using the cooler 300. After initiation of the measurement, the controller 312 selects a reagent dNTP according to the predefined sequence (S600). The solution sender 303 injects the reagent solution 108 into the cell on the ISFET array chip 1002 (S601). At this stage, the temperature of dNTP is low and DNA polymerase does not work almost at all. Thus the incorporation event hardly occurs.

(FIG. 7: Steps S602-S604)

The controller 312 heats, as a trigger for inducing the incorporation event, the well 703 and the reagent solution 108 in the well 703 using the heater 308 on the chip, thereby activating DNA polymerase (S602). The ISFET 114 measures the incorporation signal induced by the heater 308 (S603). After measuring the incorporation signal, the controller 312 injects a low temperature wash into the solution sender 303, thereby washing out the non-reacted dNTP and the reaction products, i.e. hydrogen ions and diphosphates, and cools the chip using the cooler 300 simultaneously (S604).

(FIG. 7: Steps S605-S609)

After finishing the washing process, the controller 312 selects the next dNTP (S605-S609), and then returns back to step S601 to repeat the same process. The incorporation signal measured by the ISFET 114 during the repeated process is converted into digital signals by an A/D converter included in the data processor 311 and is stored in a storage device included in the data processor 311 as measured data. The data processor 311 may identify the DNA structure according to the sequence acquired from the repeated process.

The output signal from the ISFET 114 acquired by the flowchart of FIG. 7 will be described below using FIGS. 8-10.

Figure 8:
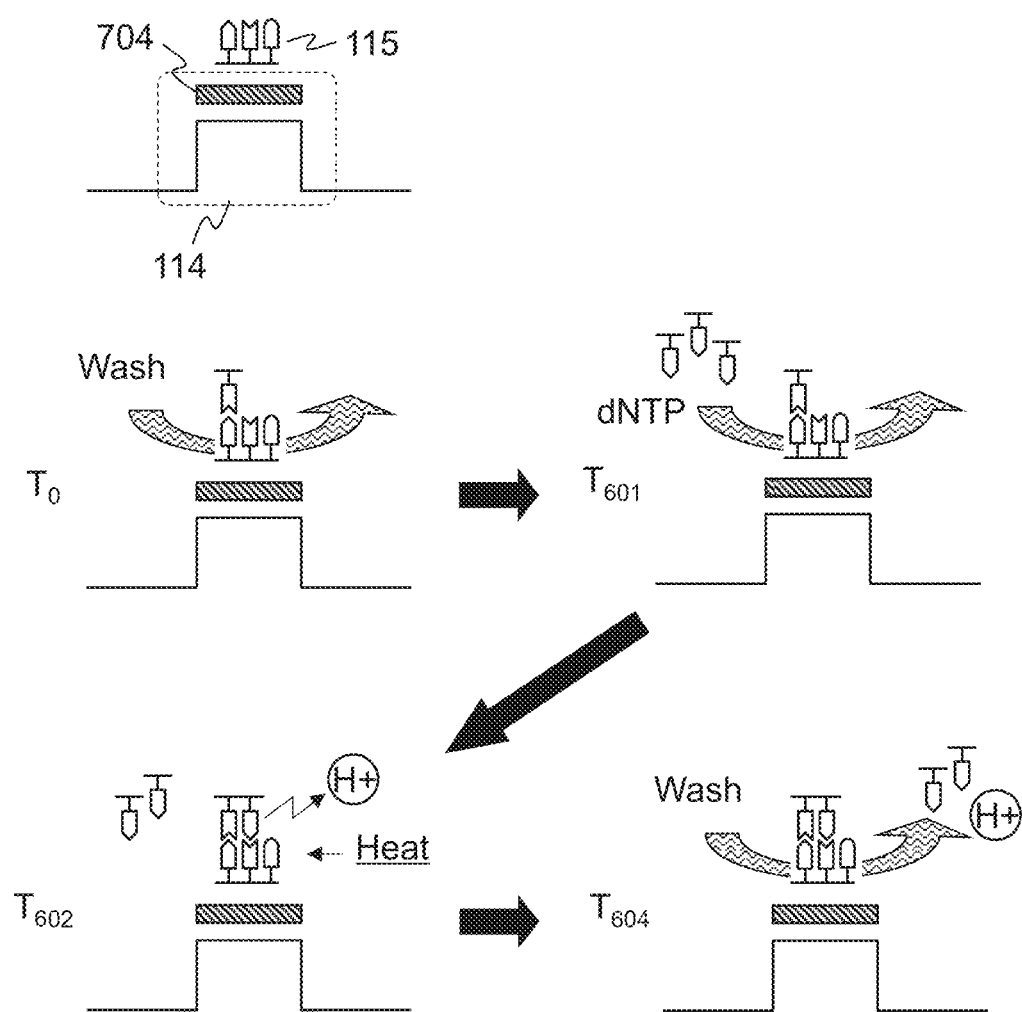
FIG. 8 is a side view diagram schematically showing one cell.

FIG. 8 is a side view diagram schematically showing one cell. FIG. 8 shows that a DNA 115 is fixed on the ISFET 114. For the sake of simplicity, the structure ranging from the ion sensitive layer 100 to the gate electrode 103 in the ISFET 114 is collectively shown as a rectangle 704.

At time $T_0$ in FIG. 8, the cell on the chip is filled with the wash and is in a cooled state. At time $T_{601}$, dNTP solution is injected into the cell as the reagent solution 108. Then the threshold voltage of the ISFET 114 varies due to various ions included in the dNTP solution and due to difference of pH between the wash and the dNTP solution. When the wash in the cell is replaced with the dNTP solution, the variation in the threshold voltage of the ISFET 114 gradually ceases. At time $T_{602}$, the dNTP solution is heated by the heater 308, and then DNA polymerase is activated. Since coupling of DNA and dNTP generates hydrogen ions and thus changes pH, the threshold voltage of the ISFET 114 varies in response to such change. At time $T_{604}$, the wash is injected and thus components of the dNTP solution and the reaction products (i.e. hydrogen ion) are washed out, and the cell is filled with the wash. Accordingly, the state returns to that of time $T_0$. By injecting the wash, the ISFET 114 is cooled to a low temperature below the optimum temperature of DNA polymerase.

Figure 9:
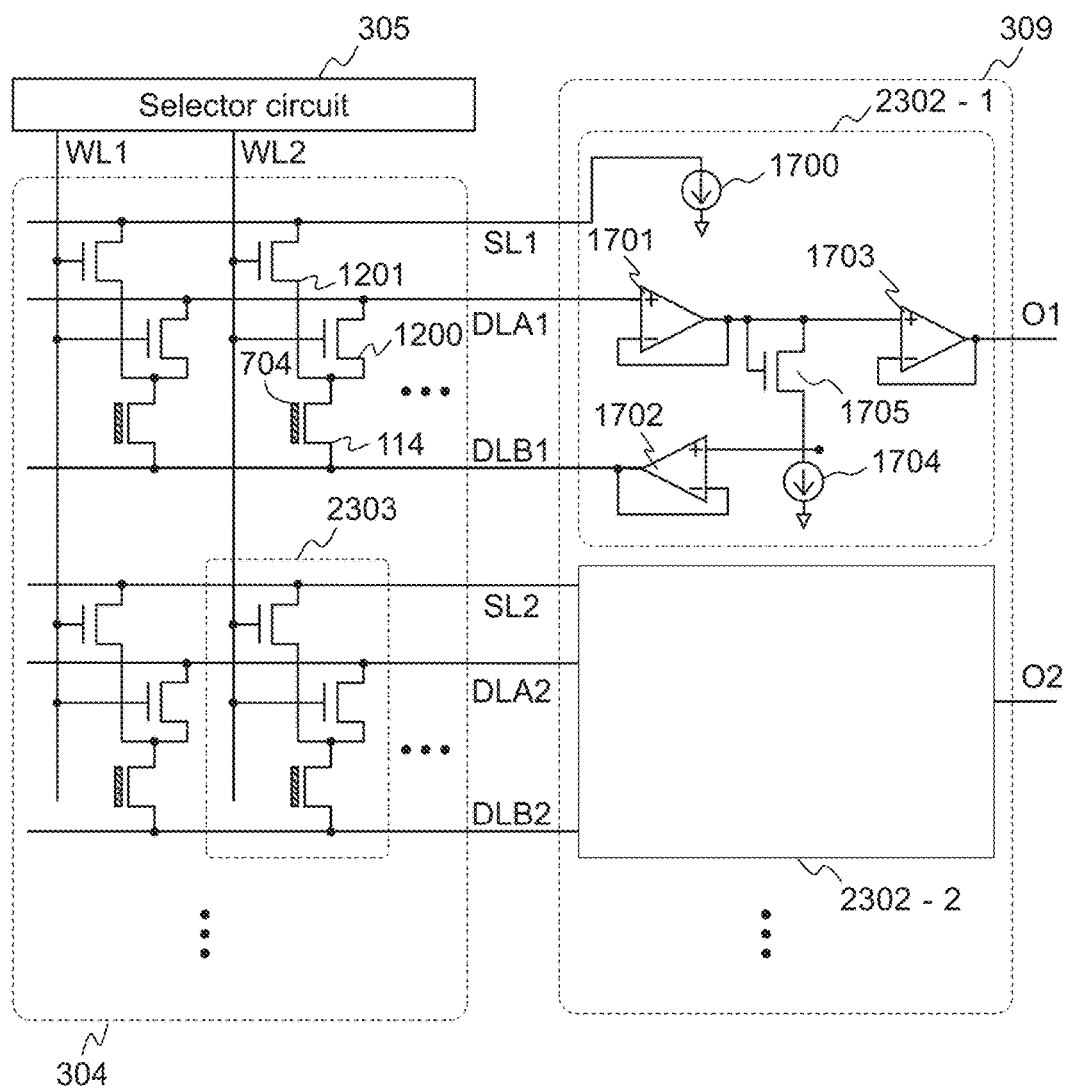
FIG. 9 is a circuit diagram showing a configuration example of the ISFET array 304, a selector circuit 305, and a reading circuit 309 included in an ISFET array chip 1002.

FIG. 9 is a circuit diagram showing a configuration example of the ISFET array 304, the selector circuit 305, and the reading circuit 309 included in the ISFET array chip 1002. The selector circuit 305 includes a typical n-bit decoder and drivers. The selector circuit 305 activates one of $2^n$ units of row selection lines WL in accordance with n units of row addresses provided from the controller 312. The ISFET array 304 includes the ISFET 114 and selection transistors for selecting the ISFET 114 allocated at intersections between the row selection lines WL and data lines DLA two dimensionally. Each cell 2303 includes two selection transistors 1200, 1201 and the ISFET 114. Each cell is connected to row selection lines WLk, source selection lines SLk, and data selection lines DLAk, DLBk. When a j-th WLj is activated to H state by a row address, the selection transistor becomes conducted in all cells connected to WLj. Then all of the ISFETs 114 on the same WLj are connected to the source lines SL and the data lines DLA respectively. FIG. 9 shows an example where all transistors are NMOS. Alternatively, all transistors may be PMOS. In this case, the logic of the row selection line WL is reversed.

The source line SLk and the data line DLAk, DLBk are connected to a k-th amplifier 2302-k in the reading circuit 309. This amplifier includes two typical current sources 1700 and 1704, two amplifiers 1701 and 1702, and an amplifier 1703 and a transistor 1705 for output. Operations of each amplifier when reading out the signal from the ISFET 114 will be described below.

The current sources 1700 and 1703 withdraw a constant current into the ground. The amplifiers 1701 and 1702 are amplifiers with voltage follower configuration and with gain of 1. The amplifiers 1701 and 1702 may be implemented by typical differential amplification circuits. These amplifiers generate, between DLAk and DLBk, a constant voltage VAB determined by the transistor 1705 and by a constant current Id flowing through the current source 1704. According to such configurations, the source-drain voltage Vds of the selected ISFET in the ISFET array is fixed approximately at VAB, and the drain current is fixed at the constant current Id determined by the current source 1700. When the ISFET 114 is working within a linear region, the drain current Id, the gate-source voltage Vgs, and the source-drain voltage Vds satisfy Equation 1 below. β is a constant unique to the ISFET 114 and Vth is the transistor threshold voltage of the ISFET 114.

$$Id = \beta\{(Vgs - Vth) - \tfrac{1}{2} \times Vds\} \times Vds \quad \text{(Equation 1)}$$

When the threshold voltage of the ISFET 114 shifts by ΔVth due to ions in the solution, Equation 2 below is satisfied assuming that the drain current Id is constant and the source-drain voltage Vds is constant by the amplifier 2302-k.

$$Id = \beta\{(Vgs' - (Vth + \Delta Vth)) - \tfrac{1}{2} \times Vds\} \times Vds \quad \text{(Equation 2)}$$

Since Id is not 0, dividing Equation 1 by Equation 2 acquires Equation 3 below.

$$Vgs' - Vgs = \Delta Vth \quad \text{(Equation 3)}$$

According to Equation 3, if the gate voltage (i.e. the voltage of the reference electrode 109) is fixed, the variation in the threshold voltage of the ISFET 114 is outputted as variation in the source voltage. Since Vds is constant, the variation in the source voltage equals to the variation in the drain voltage. Accordingly, ΔVth is outputted from the amplifier output terminal Ok. However, offset and background signal are overlapped with ΔVth. Thus as shown in FIG. 10, the incorporation signal and these noises are separated temporally by the flowchart of FIG. 7, thereby precisely retrieving the incorporation signal only.

In the circuit diagram of FIG. 9, one of the ISFETs 114 is selected by the selector circuit 305 and its output is read out by the reading circuit 309. However, as long as the number of data output pins of the ISFET array chip 1002 is sufficient, the output pins may be provided for each of the ISFETs 114. In addition, an A/D converter may be implemented on the ISFET array chip 1002 and the output from the ISFET 114 may be converted into digital data and then be outputted. In this case, the communication route from the ISFET array chip 1002 to the data processor 311 is digitized. Thus resistivity against interference noises on the route is improved.

Figure 10:
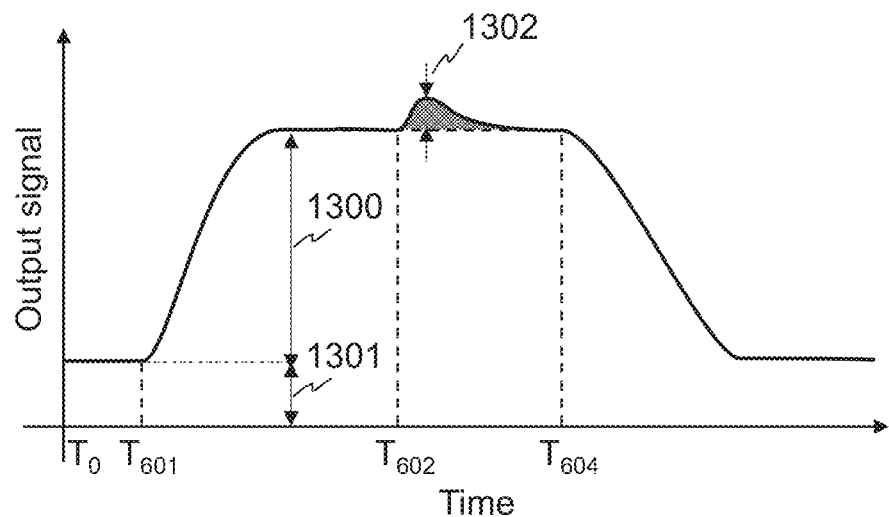
FIG. 10 is a waveform of a signal acquired by reading out a variation in threshold voltage of one of the ISFET 114 using the circuit of FIG. 9 when performing the flowchart of FIG. 7.

FIG. 10 is a waveform of a signal acquired by reading out a variation in threshold voltage of one of the ISFET 114 using the circuit of FIG. 9 when performing the flowchart of FIG. 7. As described above, when injecting dNTP solution into the cell at time $T_{601}$, the ISFET 114 outputs a signal in which a waveform component 1301 due to drift and offset and a background component 1300 are overlapped with the signal. When the cell is filled with the dNTP solution, the variation ratio of the signal gradually decreases and the signal almost saturates at some level. At time $T_{602}$ when a certain amount of time has passed from starting injection of the reagent solution 108, the heater 308 heats the reagent solution 108 to activate DNA polymerase. When DNA and dNTP are coupled with each other, hydrogen ions are generated and thus pH changes. Then the incorporation signal 1302 appears in the output signal from the ISFET 114. If the incorporation event does not occur, no hydrogen ion is generated, and thus the incorporation signal 1302 does not appear. When injecting the wash at time $T_{604}$, the components of the dNTP solution and the reaction products (i.e. hydrogen ion) are washed out and the cell is filled with the wash. Thus the signal value returns to the initial value.

In accordance with the flowchart of FIG. 7, it is possible to temporally separate the variation in the background component 1300 from the incorporation signal 1302 by providing a trigger after beginning injection of the reagent solution 108, more preferably after completing the injection of the reagent solution.

In addition, by subtracting the signal value immediately before heating by the heater 308 (i.e. the signal value including the component 1301 of drift and offset and the background component 1300) from the signal values after time $T_{602}$, it is possible to readily acquire the incorporation signal waveform without these noises.

According to the above-mentioned configurations, the background estimation using a plurality of empty wells described in Patent Literature 2 is not necessary, thereby significantly reducing the processing load. In addition, the subtraction is performed using the measured value of the ISFET 114 itself that measures the incorporation signal 1302. Thus the subtraction is not influenced by characteristic variations of the ISFET 114.

<Embodiment 1: Variations>

In the example described above, the cell is cooled using the wash and dNTP, and the cell is heated using the heater 308 on the chip to induce incorporation event. The method for controlling the temperature is not limited to above. For example, a cooling mechanism such as Peltier device may be contacted with the ISFET array chip 1002 to cool the chip. In addition, a typical heater may be contacted with the ISFET array chip 1002 to heat the chip. However, in the heating process for inducing incorporation event, it is preferable to rapidly change the temperature. This is because slow temperature change does not cause simultaneous incorporation events of copied DNAs on the bead 702, and thus the peak of the incorporation signal is not sharp.

Figure 11:
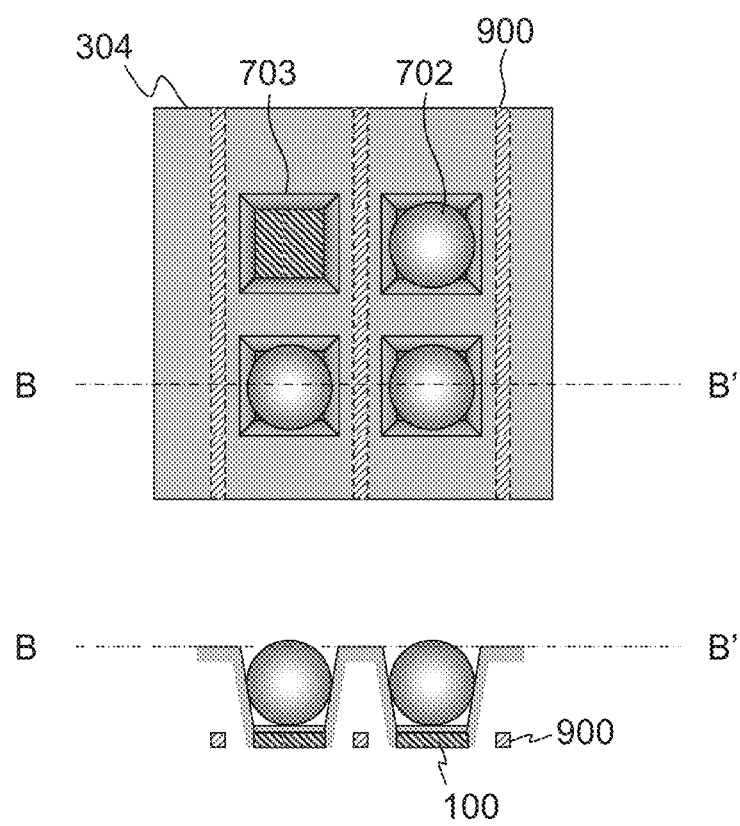
FIG. 11 is a diagram showing the ISFET array 304 and its sectional view in which a heater wiring is equipped by using semiconductor process.

FIG. 11 is a diagram showing the ISFET array 304 and its sectional view in which a heater wiring is equipped by using semiconductor process. The structures below the ion sensitive layer 100 are same as those in FIG. 1, thus omitted in the figure. The wire 900 is formed between columns of the wells 703 using semiconductor process. Electric current flows through the wire 900 to generate Joule heat, thereby heating the cell. According to such configurations, the heat source is disposed near the well 703, thus it is possible to rapidly increase the temperature in the well 703.

It is preferable if the temperature of the reagent solution 108 after the heating process is near the optimum temperature at which DNA polymerase works most effectively. The optimum temperature significantly depends on the type of DNA polymerase. For example, if DNA polymerase is Klenow Fragment the optimum temperature is around 37 degrees centigrade, and if DNA polymerase is TaqDNA polymerase the optimum temperature is 70-75 degrees centigrade. If the temperature is too high, the enzyme may be denatured to be deactivated. Thus excessive heating should be avoided. In order to avoid such excessive heating: electric current may be caused to flow through the wire 900 for a predetermined period; or the temperature sensor 307 may be installed on the ISFET array chip 1002 and the heater 308 may be controlled while monitoring the temperature so that the temperature becomes around the optimum temperature.

The example above heats DNA polymerase up to the optimum temperature to induce incorporation event of DNA. However, incorporation event may be induced by controlling the temperature above the optimum temperature down to the optimum temperature.

The trigger inducing incorporation event is not limited to temperature. For example, if the light responsive nucleotide described in JP Patent Publication (Kokai) 2009-126789 A is used as the reagent solution 108, UV irradiation at wavelength of 366 nm may be used as the trigger for incorporation event. LEDs available on the market may be used as the UV light source of wavelength 366 nm. Alternatively, the reagent solution 108 may be separated into a buffer solution that does not induce incorporation event and a dNTP reagent. The cell may be filled with the buffer solution firstly and then the dNTP reagent may be injected. In this case, the injection of dNTP reagent works as trigger. In any cases, the functional unit that generates the trigger inducing incorporation event corresponds to "trigger generator".

In FIG. 8, after injecting dNTP solution at time $T_{601}$, the timing $T_{602}$ for inducing incorporation event may be determined as below. A method for determining the timing may be: a time $T_{SAT}$, from a time point when injecting dNTP solution to a time point when the variation in the background signal becomes sufficiently small, is measured in advance experimentally; and the controller 312 is programmed to generate the trigger of incorporation event when $T_{SAT}$ has passed from $T_{601}$. Another method may be: monitoring the background signal waveform; and automatically detecting a time point when the variation in the background signal waveform converges. The latter method will be described using FIG. 12 below.

Figure 12:
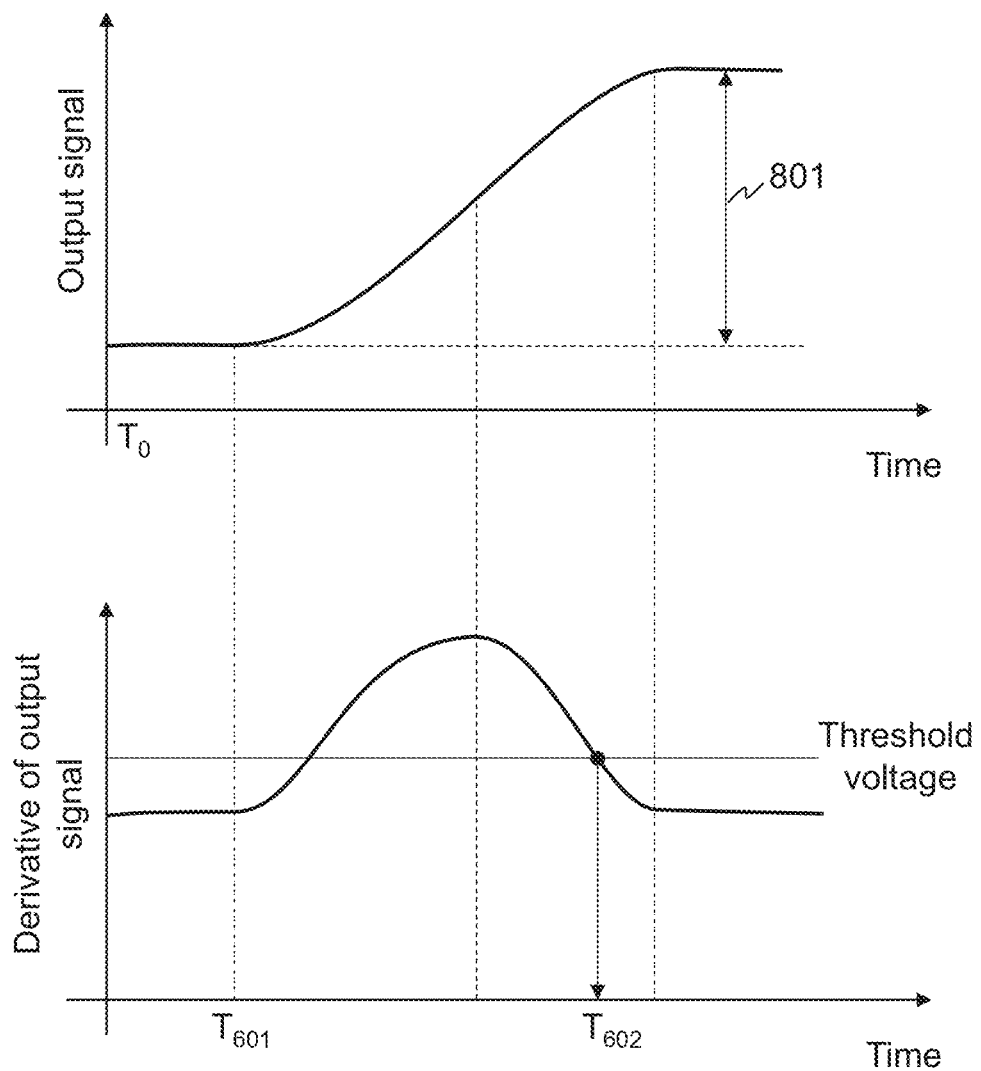
FIG. 12 is a diagram showing a temporal variation of a background signal waveform and its derivative.

FIG. 12 is a diagram showing a temporal variation of a background signal waveform and its derivative value. The controller 312 differentiates the background signal waveform. The time at which the calculated difference becomes below a preconfigured threshold may be employed as time $T_{602}$. In this case, when the amount of variation in the background signal becomes below a target level, the incorporation event may be initiated immediately, thereby reducing the time required for the measuring flow. The differentiation of the signal waveform may be implemented by typical differentiation circuits comprising an inverse amplifier and a capacitor. The threshold comparison may be performed by typical voltage comparison circuits. Alternatively, software on the data processor 311 may differentiate the waveform and may compare the threshold.

FIG. 13 is a diagram showing a configuration example in a case where background is removed using some of the ISFETs 114 on the ISFET array chip 1002. It is not always necessary use all of the ISFETs 114 to detect the background. The background may be detected using only the ISFET 114 located at downstream side in the direction to which the reagent solution 108 flows.

As shown in FIG. 13(a), it is assumed that: a dNTP solution 1101 is injected from an inlet 1103 to the cell filled with a wash 1102; and the wash 1102 and the dNTP solution are discharged from an outlet 1104. In this case, $T_{602}$ may be determined according to background waveforms of one or more of the ISFETs 114 located at a position closer to the outlet 1104 than to the inlet 1103, i.e. at downstream side of the reagent flow. This is because if the variation in background waveform is converged at downstream side, it is possible to determine that exchanging the solution has been completed across the ISFET array chip 1003. As shown in FIG. 9, when driving the ISFET 114 using current sources, the number of ISFET 114 through which electric current flows is increased due to increase in the number of parallel arrays, which incurs increase in electric power consumption. By restricting the number of ISFET 114 used for measuring the background as above, it is possible to significantly reduce power consumption of the chip. In addition, it is possible to reduce amount of calculation required for the differentiation process.

As shown in FIG. 13(b), a cell 1105 dedicated to measure the background may be installed at downstream side of the ISFET array chip 1002. In this case, it is preferable to provide, in addition to the reading circuit 309, a circuit for retrieving the background from the cell 1105.

Figure 14:
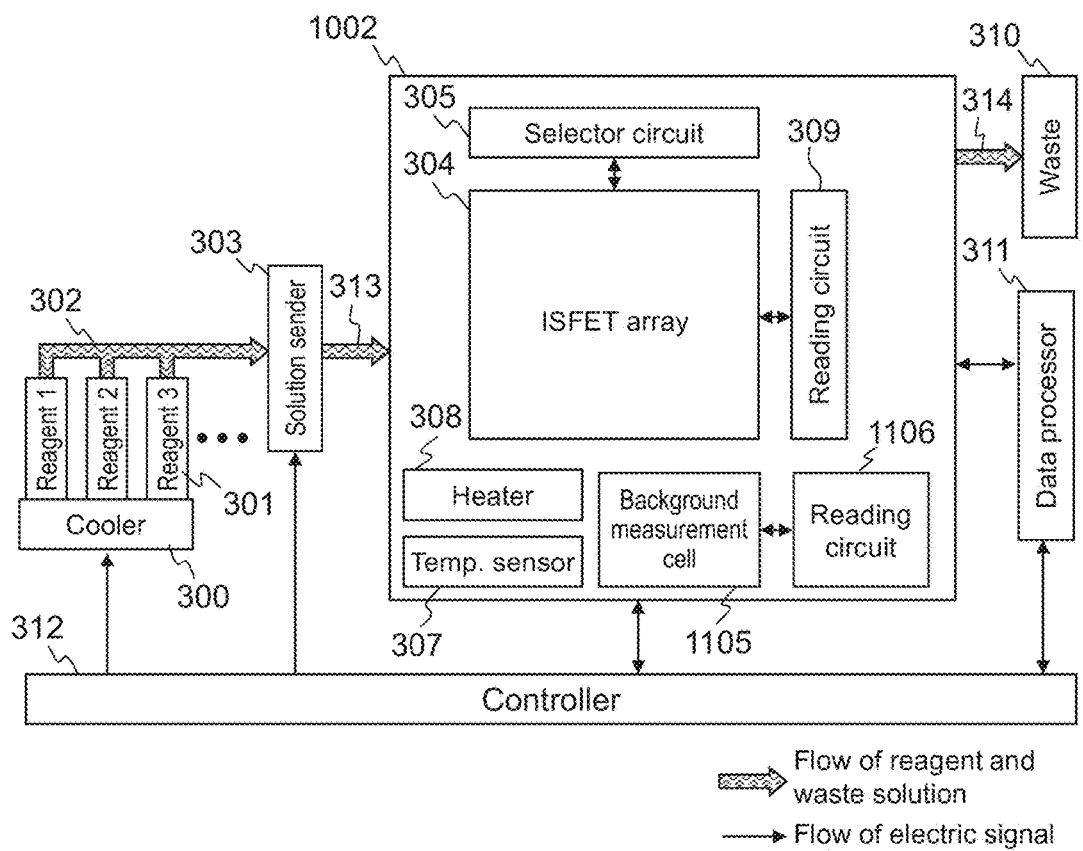
FIG. 14 is a circuit diagram including a reading circuit 1106 that reads out signals outputted from a cell 1105 shown in FIG. 13.

FIG. 14 is a circuit diagram including a reading circuit 1106 that reads out signals outputted from the cell 1105 shown in FIG. 13. The reading circuit 1106 is a dedicated circuit that is independent from the reading circuit 309. Other circuit configurations are same as those of FIG. 5. According to the circuit configuration shown in FIG. 14, it is not necessary when measuring the background to operate the selector circuit 305 or to operate the reading circuit 309 including a lot of current sources. Thus it is possible to further reduce power consumption.

<Embodiment 1: Summary>

As discussed thus far, the biomolecule measuring device according to the embodiment 1 generates a trigger for the reagent solution 108 to react using the heater 308 or other alternative means, after the solution sender 303 starts transmitting the reagent solution 108 or more preferably after the solution sender 303 completes transmission of the reagent solution 108. Accordingly, it is possible to temporally separate the incorporation signal 1302 from the background as shown in FIG. 10, thereby readily extracting the incorporation signal 1302 only.

The biomolecule measuring device according to the embodiment 1 includes a circuit that fixes the drain current of ISFET 114 at Id and that fixes the source-drain voltage Vds at VAB. Accordingly, as shown in Equation 3, it is possible to extract only the threshold variation ΔVth of the ISFET 114 from the output terminal Ok.

The biomolecule measuring device according to the embodiment 1 is capable of subtracting the drift and offset component 1301 and the background component 1300 detected by each of the ISFET 114, by using the signals outputted from each of the ISFETs 114 only. Accordingly, it is possible to suppress computational loads for detecting the background. Further, the data value range is narrowed by suppressing the offset range. Thus it is possible to reduce conversion precision of A/D converter and amount of data.

<Embodiment 2>

The embodiment 1 performs subtracting calculation in which the drift and offset component 1301 and the background 1300 are subtracted from the signal waveform detected by the ISFET 114, thereby extracting the incorporation signal 1302 only. An embodiment 2 of the present invention describes another configuration example for subtracting the drift and offset component 1301 and the background 1300.

Figure 15:
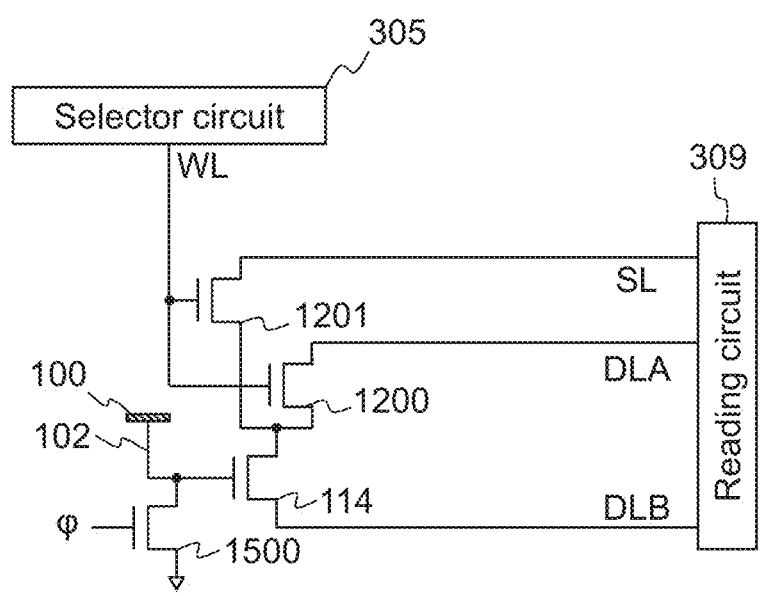
FIG. 15 is a circuit diagram in which one cell and its peripheral circuits are extracted from the ISFET array chip 1002 included in the biomolecule measuring device according to an embodiment 2.

FIG. 15 is a circuit diagram in which one cell and its peripheral circuits are extracted from the ISFET array chip 1002 included in the biomolecule measuring device according to the embodiment 2. Although not shown in the figure, there are a plurality of row selection lines WL, source lines SL, and data lines DLA, DLB as in FIG. 9. Regarding the ISFET 114, the ion sensitive layer 100 and the floating gate 102 only are schematically shown and the protection layer 101 is omitted in the figure.

In the embodiment 2, the floating gate 102 is connected to a voltage source (such as ground) via a transistor 1500. The voltage source fixes the voltage of a gate input 102 of the ISFET 114 and is not necessarily a ground. The transistor 1500 is controlled by a driving signal φ generated by the controller 312. The transistor 1500 turns ON/OFF the connection between the floating gate 102 and the voltage source. Other configurations are same as those of the embodiment 1.

Figure 16:
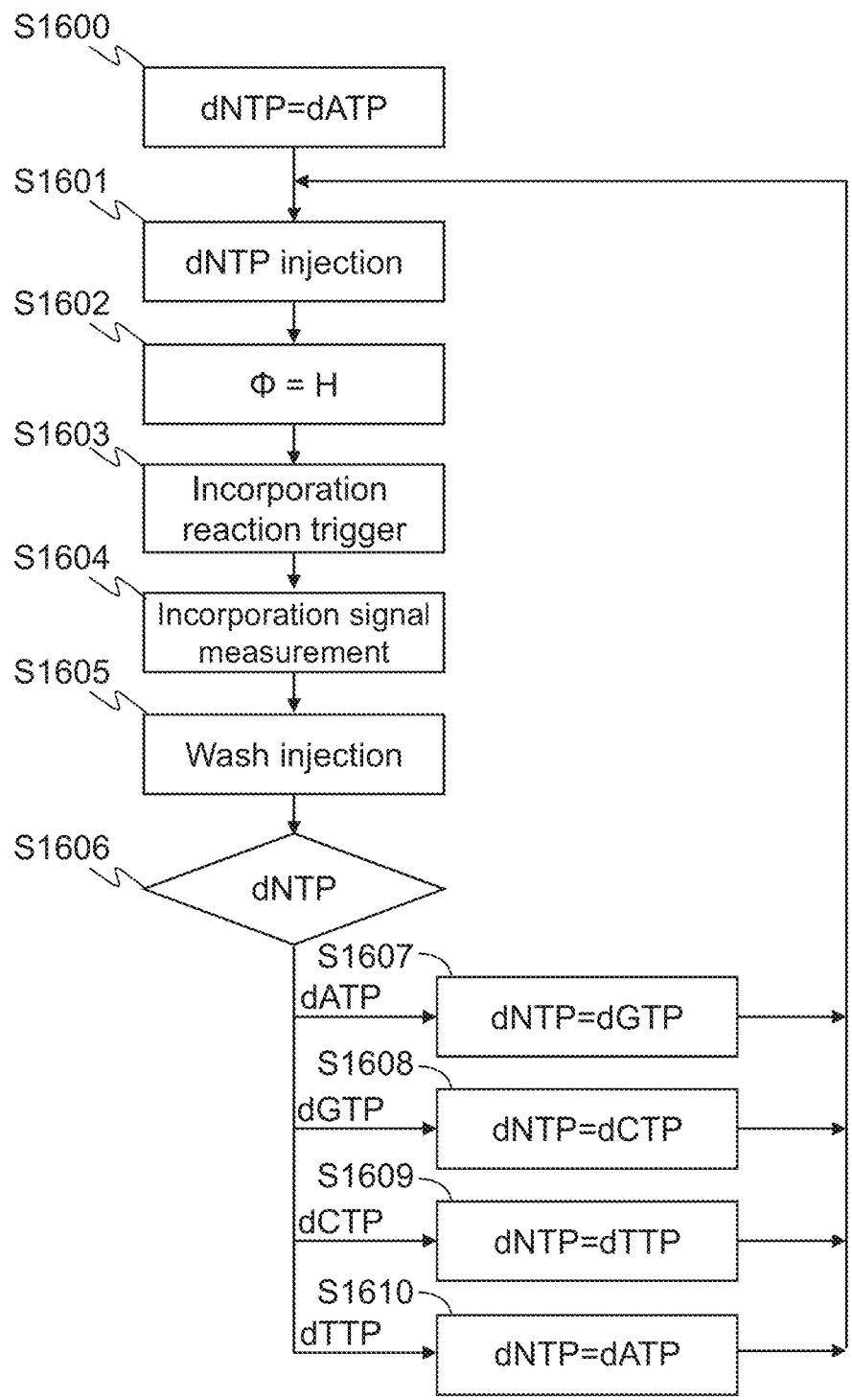
FIG. 16 is a flowchart in which the biomolecule measuring device according to the embodiment 2 determines DNA sequences.

FIG. 16 is a flowchart in which the biomolecule measuring device according to the embodiment 2 determines DNA sequences. Hereinafter, each step in FIG. 16 will be described.

(FIG. 16: Steps S1600-S1601)

Figure 17:
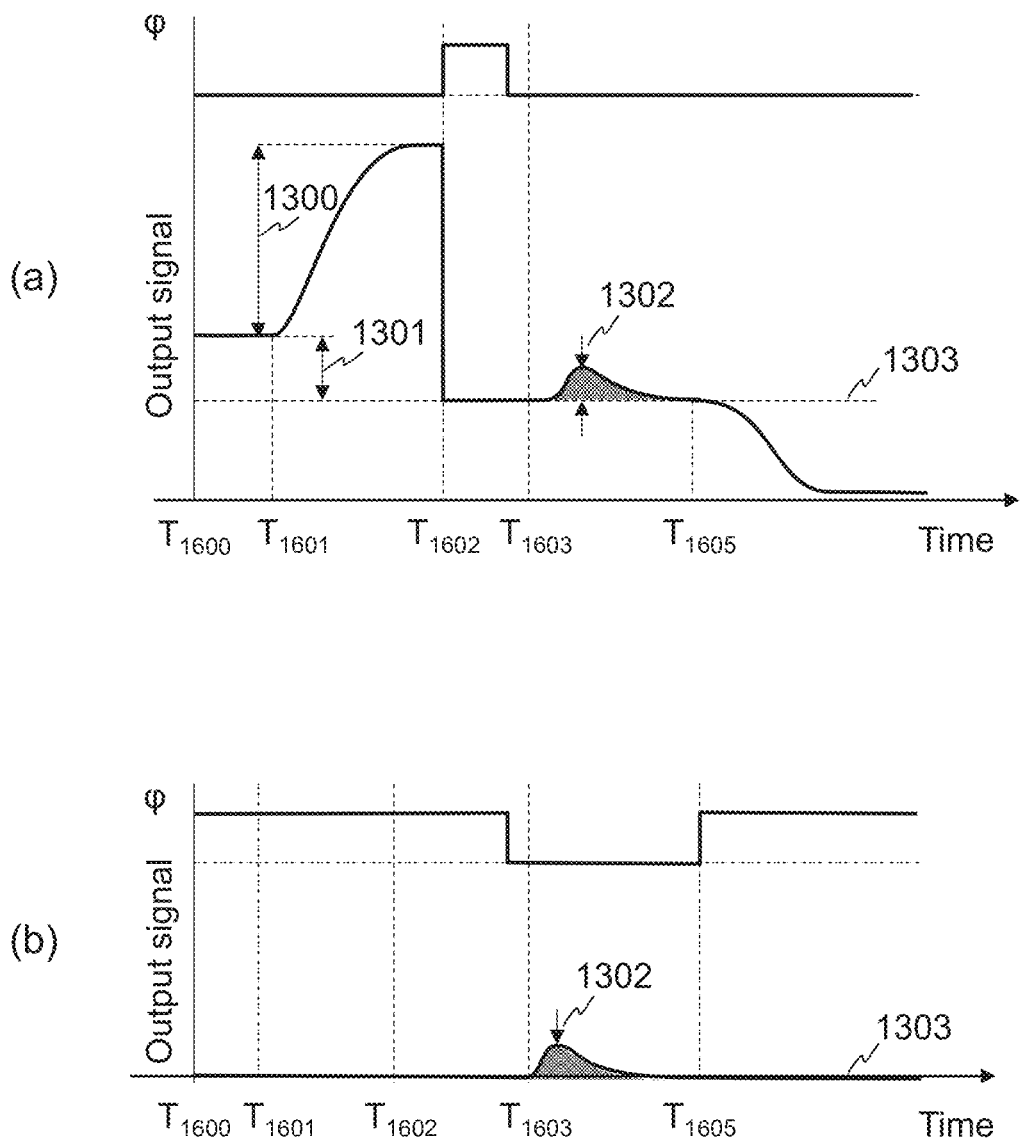
FIG. 17 is a waveform of a signal acquired by reading out a variation in threshold voltage of one of the ISFET 114 using the circuit of FIG. 15 when performing the flowchart of FIG. 16.

These steps are same as steps S600-S601 in FIG. 7. After step S1600, the background 1300 and the drift and offset component 1301 are detected as shown in FIG. 17 later.

(FIG. 16: Step S1602)

The controller 312 applies a Hi signal as the driving signal φ for the transistor 1500. When the transistor 1500 is turned ON, the voltage of the floating gate 102 is fixed at ground voltage. Accordingly, the background 1300 and the drift and offset component 1301 are reset. After these noises are reset, the controller 312 turns OFF the transistor 1500. The signal waveform detected by the ISFET 114 in this step will be described in FIG. 17 later.

(FIG. 16: Steps S1603-S1610)

These steps are same as steps S602-S609 in FIG. 7. After step S1610, the process returns back to step S1601 to repeat the same process.

FIG. 17 is a waveform of a signal acquired by reading out a variation in threshold voltage of one of the ISFET 114 using the circuit of FIG. 15 when performing the flowchart of FIG. 16. After step S1601, the ISFET 114 detects the background 1300 and the drift and offset component 1301 as shown at time $T_{1601}$ in FIG. 17(a). When the controller 312 performs step S1602 at time $T_{1602}$, the signal detected by the ISFET 114 is reset into a signal reference point 1303. It is preferable if the time at which the transistor 1500 is turned ON is between when the background 1300 becomes stable and when the incorporation event trigger is supplied.

As shown in FIG. 17(a), the output signal from the ISFET 114 does not include the drift and offset component 1301 and the background component 1300, and includes the incorporation signal 1302 only. Accordingly, it is not necessary for the data processor 311 to subtract these noises, thereby further reducing processing loads. In addition, the crest value of the signal outputted from the ISFET array chip 1002 is suppressed down to a low value. Thus it is possible to decrease the dynamic range required for the A/D converter. In addition, the amount of data is reduced and thus it is possible to save the data storage area.

FIG. 17(b) shows a modified example of the driving signal φ. As shown in the figure, the driving signal φ may be Hi when injecting dNTP solution and when washing the cell, and the driving signal φ may be Lo only when measuring the incorporation signal 1302. Accordingly, the output value from the ISFET 114 is fixed at the signal reference point 1303 except when measuring the incorporation signal 1302, thereby eliminating rapid signal change. Thus it is possible to further reduce noises.

In FIG. 17(b), the transistor 1500 should be turned OFF at least when acquiring the incorporation signal 1302. Therefore, for example, the driving signal φ may be set Lo after inputting the incorporation event trigger to start the heating process and before reaching the optimum temperature. In addition, when promoting the incorporation event by irradiating UV, the driving signal φ may be set Lo after irradiating UV for a certain amount of time. Accordingly, it is possible to reduce influences by which the output from the ISFET 114 is modulated due to high energy light of the UV light source.

<Embodiment 2: Summary>

As discussed thus far, the biomolecule measuring device according to the embodiment 2 includes the transistor 1500 that turns ON/OFF the connection between the floating gate 102 and the voltage source. The biomolecule measuring device turns ON the transistor 1500 before measuring the incorporation signal 1302 to reset the noises. Accordingly, the process for subtracting the noise components is not necessary, thereby reducing the computational loads of the data processor 311. In addition, it is possible to decrease the dynamic range of A/D converter and amount of data.

The embodiment 2 outputs the incorporation event trigger to measure the incorporation signal 1302 after resetting the noises using the transistor 1500. However, even if the incorporation event trigger is not used, it is possible to cancel the drift and offset component 1301 using the transistor 1500. In this case, the temperature sensor 307, the heater 308, and the cooler 300 are not necessary, thereby simplifying the system configuration. In this case, the driving sequence of the biomolecule measuring device corresponds to the flowchart of FIG. 16 excluding step S1603.

<Embodiment 3>

The embodiments 1-2 describe configuration examples where the drift and offset component 1301 and the background component 1300 are removed, thereby improving the signal quality of the ISFET 114. An embodiment 3 of the present invention describes a configuration example where the signal quality of the ISFET 114 is improved by other means.

Figure 18:
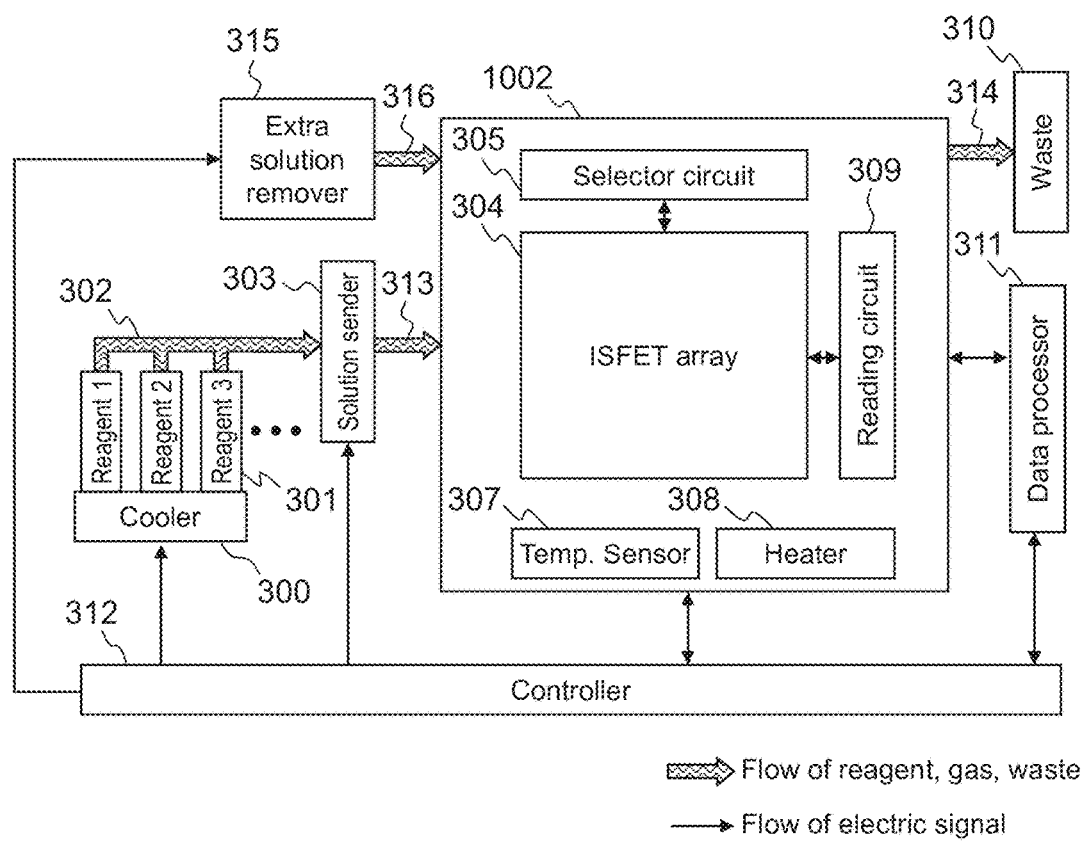
FIG. 18 is a functional block diagram of the biomolecule measuring device according to an embodiment 3.

FIG. 18 is a functional block diagram of the biomolecule measuring device according to the embodiment 3. The biomolecule measuring device according to the embodiment 3 includes an extra solution remover 315 in addition to the configuration described in the embodiment 2. Other configurations are same as those of the embodiment 2. Thus hereinafter differences will be mainly described.

The extra solution remover 315 is a device that removes reagent solutions outside the well 703. The extra solution remover 315 is controlled by the controller 312. The extra solution remover 315 may be implemented by pumps for sending a medium 1107 into the cell described in FIG. 19 later. The medium 1107 is supplied via a reagent solution route 316.

Figure 19:
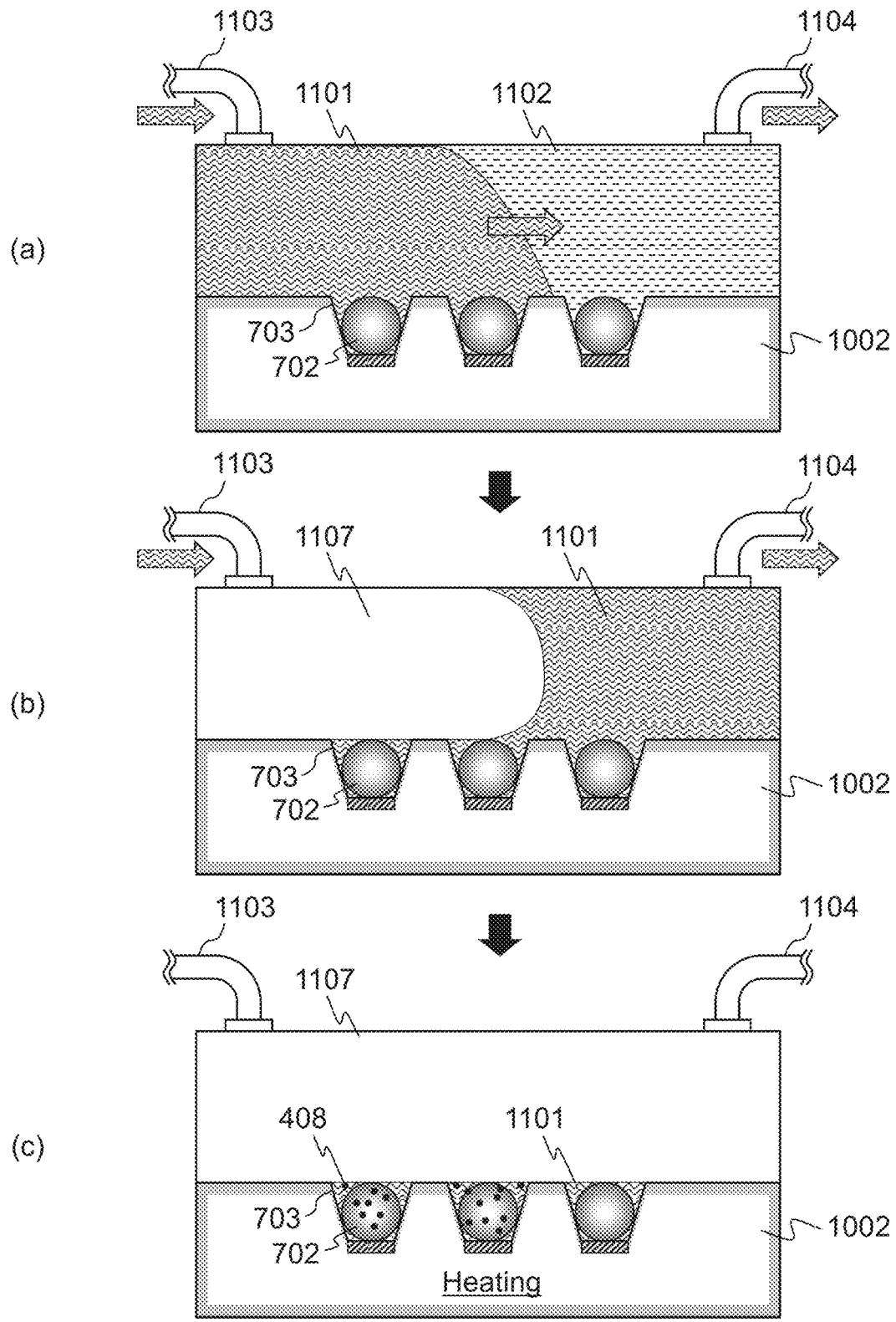
FIG. 19 is a side sectional diagram of a well 703.

FIG. 19 is a side sectional diagram of the well 703. Hereinafter, operations of the extra solution remover 315 will be described using FIG. 19.

In FIG. 19(a), the solution sender 303 injects the dNTP solution 1101 from the inlet 1103 into the cell filled with the wash 1102, and discharges the wash 1102 from the outlet 1104. In FIG. 19(b), the extra solution remover 315 injects the medium 1107 from the inlet 1103 into the cell, and discharges the extra dNTP 1101 outside the well 703 from the outlet 1104. When the extra dNTP solution 1101 is discharged, the dNTP solution 1101 outside the well 703 is removed as shown in FIG. 19(c). When the heater 308 heats the cell under the state shown in FIG. 19(c), the hydrogen ion 408 is generated.

Figure 20:
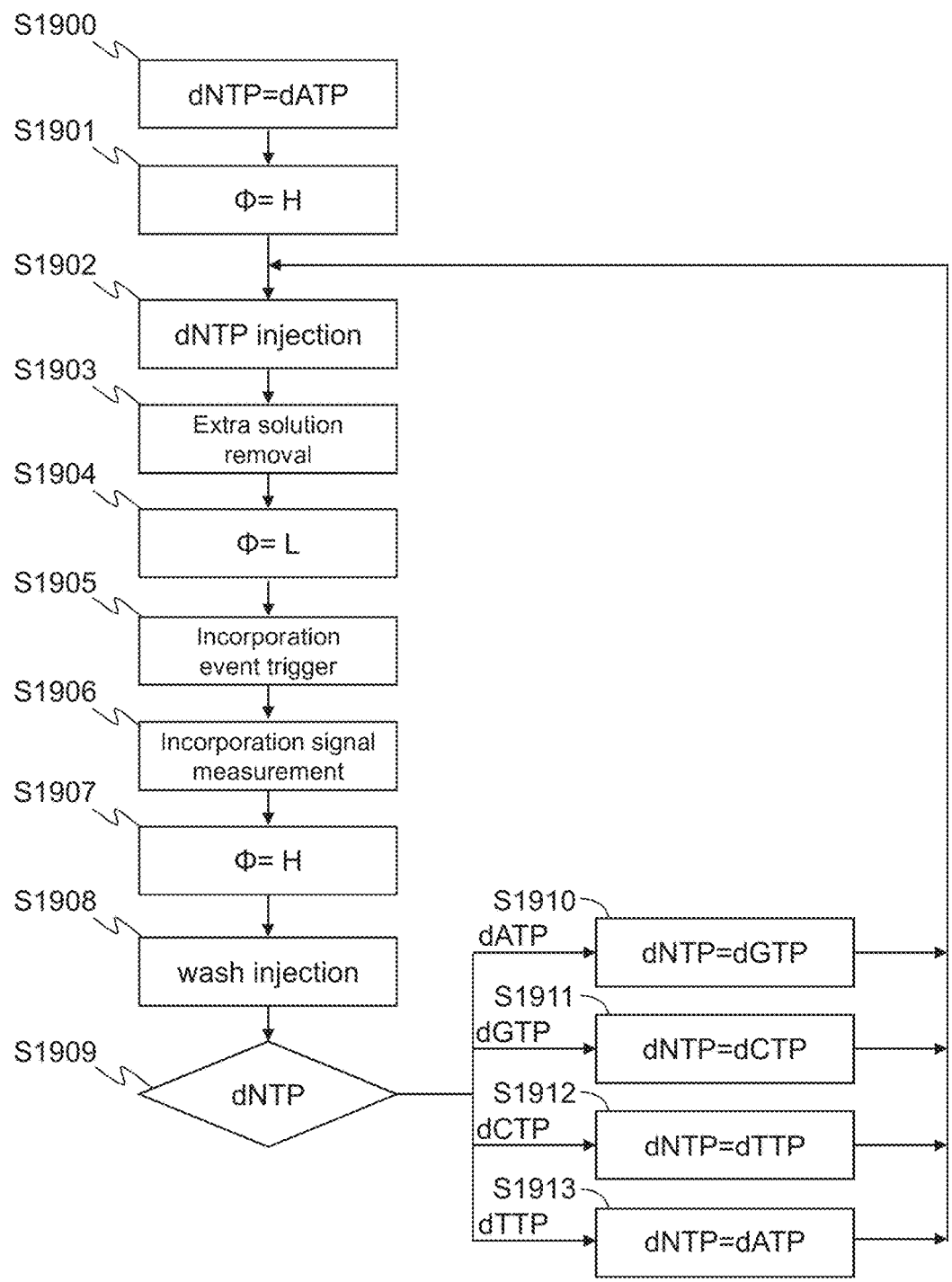
FIG. 20 is a flowchart in which the biomolecule measuring device according to the embodiment 3 determines DNA sequences.

FIG. 20 is a flowchart in which the biomolecule measuring device according to the embodiment 3 determines DNA sequences. Hereinafter, each step in FIG. 20 will be described.

(FIG. 20: Steps S1900-S1902)

These steps are same as steps S1600-S1602 in FIG. 16. However, considering the returning point from steps S1910-S1913, step S1901 is previously performed for setting the driving signal φ at Hi. The transistor 1500 is ON in step S1902, thus the drift and offset component 1301 and the background component 1300 are reset.

(FIG. 20: Step S1903)

The controller 312 drives the extra solution remover 315 to discharge the extra dNTP solution 1101 outside the well 703 from the outlet 1104, as shown in FIG. 19(b). In order to keep the dNTP solution 1101 only in the well 703, it is preferable to use the medium 1107 that is not mixed with the dNTP solution 1101 and that has a specific gravity lighter than that of the dNTP solution 1101. For example, it is preferable to use inert gases such as air, nitrogen, or argon or to use oil.

(FIG. 20: Steps S1904-S1913)

These steps are same as steps S1603-S1610 in FIG. 16. However, this flowchart sets the driving signal φ at Hi in step S1901 outside the loop. In order to comply with such process configuration, the driving signal φ is switched between Lo and Hi in steps S1904 and S1907 respectively before and after the incorporation event trigger.

The extra solution remover 315 separates each of the wells 703 during incorporation event of DNA. Thus it is possible to prevent the hydrogen ion 408 from spreading between the wells 703. In other words, it is possible to prevent cross talks between adjacent wells. In addition, the dNTP solution 1101 only exists in the well 703. Thus it is possible to prevent the generated hydrogen ion 408 from spreading to outside of the well 703 or from being vanished due to buffer effect of the solution outside of the well 703, thereby preventing the output signal of the ISFET 114 from being diminished. Accordingly, it is expectable to increase the crest value of the incorporation signal 1302 to improve the duration of signal.

If each of the wells 703 is separated from each other by removing the extra dNTP solution 1101, the connectivity between the reference electrode 109 and the dNTP solution 1101 in the well 703 may be degraded. In such cases, the reference electrode 109 may be installed in each of the wells 703 individually.

In order to readily remove the extra dNTP solution 1101, the substrate surface of the ISFET array chip 1002 may be coated with material that is water-repellent against the dNTP solution 1101. Accordingly, it is possible to reduce possibility with which the extra dNTP solution 1101 is not removed from the substrate surface. The water-repellency of the coat material would be effective enough as long as it promotes the extra dNTP solution 1101 to be removed. Specifically, fluorochemical coating agents available on the market, such as Teflon (registered trademark, DuPont) or CYTOP (registered trademark, Asahi Glass), may provide the water-repellency. Further, it is possible to increase the water-repellency by processing concavity and convexity on the surface.

<Embodiment 3: Variations>

Figure 21:
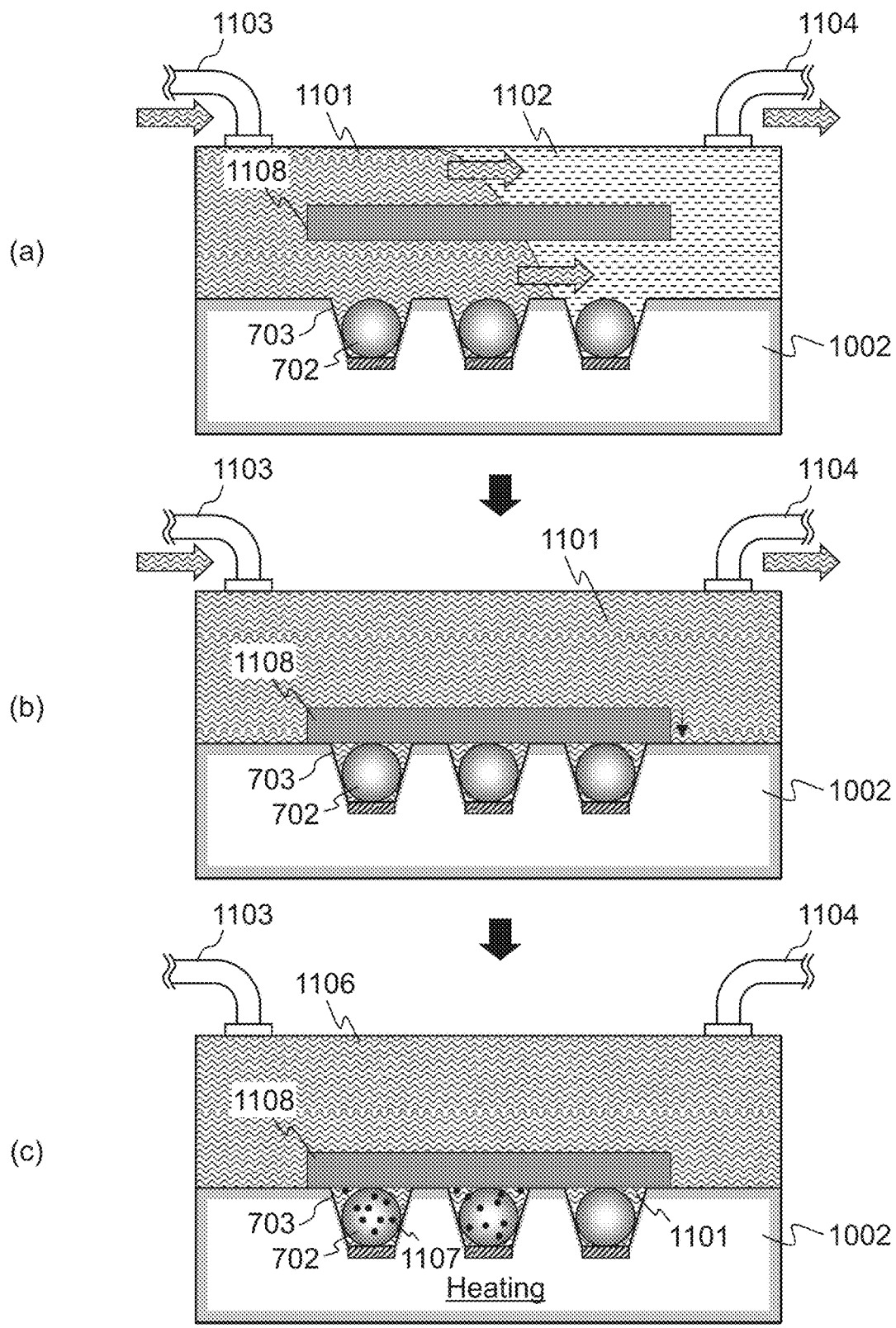
FIG. 21 is a diagram showing another configuration example in which each of the wells 703 is separated from each other.

FIG. 21 is a diagram showing another configuration example in which each of the wells 703 is separated from each other. In FIG. 21, instead of removing the extra dNTP solution 1101 by the medium 1107, each of the wells 703 is lidded using a structure 1108. Accordingly, it is possible to separate each of the wells 703 without adding the medium 1107.

Figure 22:
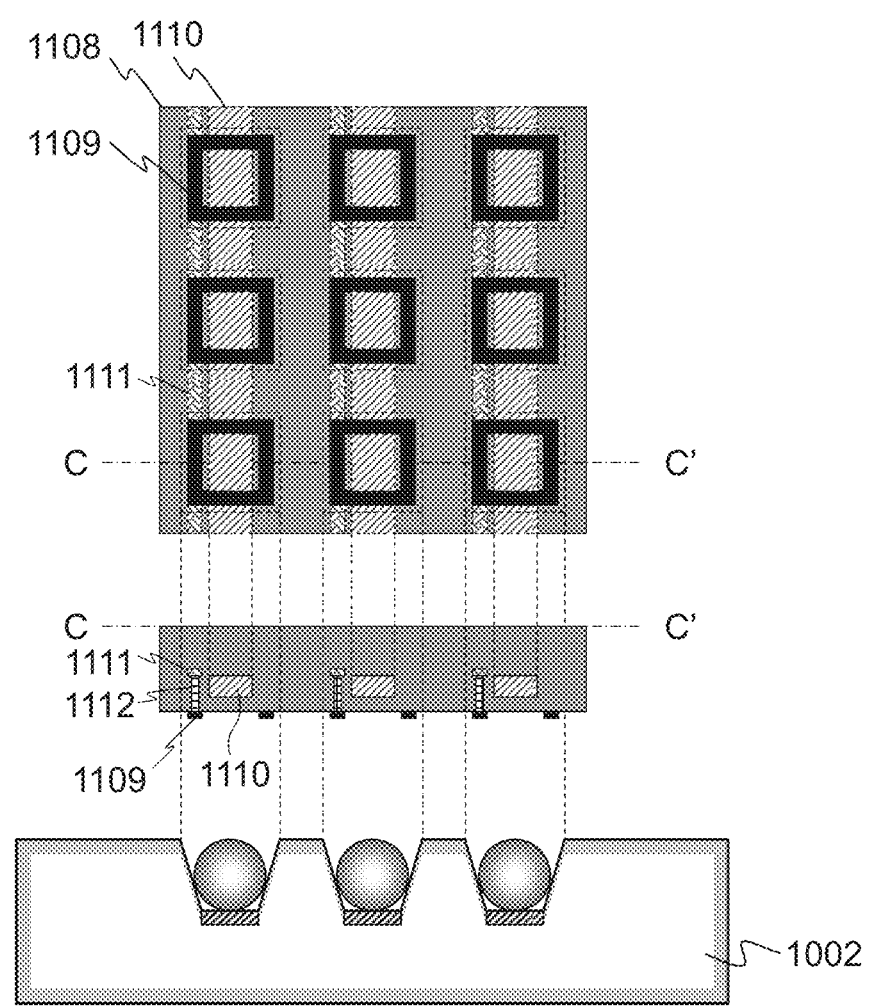
FIG. 22 is a diagram showing an internal architecture of a structure 1108.

FIG. 22 is a diagram showing an internal architecture of the structure 1108. As shown in FIG. 22, it is possible to more rapidly heat the solution in the well 703 by adding a heater 1110 in the structure 1108. In addition, a reference electrode 1109 may be provided in the structure 1108 and the reference electrode 1109 may be connected to other circuit units via wires 1111 and 1112. Further, the surface of the structure 1108 may be coated with material that is water-repellent against the dNTP solution 1101. Accordingly, it is possible to further reduce the possibility with which the extra dNTP solution 1101 is not removed from the substrate surface.

<Embodiment 3: Summary>

As discussed thus far, the biomolecule measuring device according to the embodiment 3 separates each of the wells 703 from each other to prevent the signal components from interfering between adjacent wells 703 due to cross talks. Thus it is possible to improve the signal quality of the ISFET 114.

The present invention is not limited to the embodiments, and various modified examples are included. The embodiments are described in detail to describe the present invention in an easily understood manner, and the embodiments are not necessarily limited to the embodiments that include all configurations described above. Part of the configuration of an embodiment can be replaced by the configuration of another embodiment. The configuration of an embodiment can be added to the configuration of another embodiment. Addition, deletion, and replacement of other configurations are also possible for part of the configurations of the embodiments.

For example, the embodiments 1-3 describe examples that measure reactions of sample DNAs fixed on the bead 702. As a modified example for fixing DNA, DNA may be fixed in the well 703 which surface is chemically modified. Accordingly, it is possible to reduce a possibility with which the bead 702 and the sample DNA are washed away when exchanging the solution.

The present invention is not limited to measuring devices that identify structures of DNA samples. The present invention may be applied to general measuring devices that detect ions generated by reactions between biomolecule samples and reagents. ISFET is described as a semiconductor sensor that detects ions. However, other sensors may be used as long as providing same functionalities.

REFERENCE SIGNS LIST 100 ion sensitive layer
101 protection layer 102 floating gate
103 gate electrode
104 gate oxide
105 drain
106 source
107 Si substrate
108 reagent solution
109, 1109 reference electrode
110 substrate contact
111, 112, 113, 703 well
114 ISFET
115 DNA
116 cell
300 cooler
301 reagent container
302, 313, 314, 316 reagent solution route
303 solution sender
304 ISFET array
305 selector circuit
307 temperature sensor
308, 1110 heater
309 reading circuit
310 waste solution
311 data processor
312 controller
315 extra solution remover
1002 ISFET array chip
1003, 1701, 1702, 2302 amplifier
1101 dNTP solution
1102 wash
1103 inlet
1104 outlet
1105 background measuring cell
1106 reading circuit
1107 medium
1108 structure
1111, 1112 wire
1200, 1201 selection transistor
1300 background component
1301 drift and offset component
1302 component derived from incorporation event
1303 signal reference level
1500 transistor
1700, 1703, 1704 current source
1705 transistor
2303 cell
DLA, DLA1, DLAk, DLB, DLB1, DLBk data line
O1, O2, Ok amplifier output terminal
SL, SL1, SL2, SLk source line

The invention claimed is:

1. A biomolecule measuring device comprising:
a semiconductor sensor that has a biomolecule sample disposed thereon and measures a concentration of an ion generated from a chemical reaction of the biomolecule sample;
a solution sender that transmits a reagent that undergoes the chemical reaction with the biomolecule sample to generate the ion;
a trigger generator that generates a physical environment that induces the chemical reaction;
a controller that is programmed to control an operation of the solution sender and of the trigger generator; and
a processor that is programmed to identify a configuration of the biomolecule sample,
wherein the semiconductor sensor comprises an ion sensitive layer which produces an interface voltage that changes due to the ion, and a transistor that has a gate electrode coupled to the ion sensitive layer, a source terminal and a drain terminal, the source terminal being configured to output electric signals caused by a variation in the interface voltage,
wherein a reading circuit is connected to the transistor, and includes a current source configured to keep a drain current of the transistor constant and a circuit configured to keep a source-drain voltage of the transistor constant,
wherein the reading circuit is configured to extract a variation in a threshold voltage of the transistor from a variation in a source voltage of the source terminal, and output the variation in the threshold voltage,
wherein the controller is further programmed to control the solution sender and the trigger generator so that the solution sender starts transmitting the reagent onto the biomolecule sample disposed on the semiconductor sensor and the trigger generator generates the physical environment after the solution sender starts transmitting the reagent onto the biomolecule sample disposed on the semiconductor sensor, and
wherein the processor is further programmed to execute a difference calculation which subtracts a first measured result corresponding to the variation in the threshold voltage of the transistor in a first period from when the solution sender starts transmitting the reagent to when the trigger generator generates the physical environment after the solution sender starts transmitting the reagent from a second measured result corresponding to the variation in the threshold voltage of the transistor in a second period after the trigger generator generates the physical environment to identify the configuration of the biomolecule sample.

2. The biomolecule measuring device according to claim 1,
wherein the controller is further programmed to control the solution sender and the trigger generator to repeat an operation of transmitting the reagent while exchanging a plurality of types of the reagent and an operation of generating the physical environment, and
wherein the processor is further programmed to identify the configuration of the biomolecule sample according to each difference calculation acquired in the repeated operations.

3. The biomolecule measuring device according to claim 2,
wherein the difference calculation removes noise due to drift and offset and noise due to the reagent from the second measured result.

4. The biomolecule measuring device according to claim 3,
wherein the semiconductor sensor is an ISFET array including a plurality of cells,
and wherein the processor is further programmed to execute the difference calculation separately for each one of the respective cells using only the first and second measured results of the respective one of the cells.

5. The biomolecule measuring device according to claim 3,
wherein the semiconductor sensor includes a concave portion that receives the biomolecule sample and the reagent,
wherein the ion sensitive layer is connected to a bottom of the concave portion, and
wherein a lid seals the concave portion.

6. The biomolecule measuring device according to claim 5,
wherein the trigger generator is attached to the lid, and
wherein the trigger generator generates the physical environment so that the reagent sealed in the concave portion induces the chemical reaction.

7. The biomolecule measuring device according to claim 2,
wherein the processor is further programmed to calculate a temporal differential value of the first measured result, and
wherein the controller is further programmed to control the trigger generator to generate the physical environment at a time point when the temporal differential value is at or below a predetermined threshold.

8. The biomolecule measuring device according to claim 1,
wherein the trigger generator generates the physical environment by controlling a temperature of the reagent or by irradiating an ultraviolet ray onto the reagent.

9. The biomolecule measuring device according to claim 1,
wherein the solution sender transmits the reagent that causes the chemical reaction after transmitting a buffer solution that does not cause the chemical reaction onto the semiconductor sensor.

10. A biomolecule measuring device comprising:
a semiconductor sensor that has a biomolecule sample disposed thereon and measures a concentration of an ion generated from a chemical reaction of the biomolecule sample;
a solution sender that transmits a reagent that undergoes the chemical reaction with the biomolecule sample to generate the ion;
a trigger generator that generates a physical environment that induces the chemical reaction;
a controller that is programmed to control an operation of the solution sender and of the trigger generator; and
a processor that is programmed to identify a configuration of the biomolecule sample,
wherein the semiconductor sensor comprises an ion sensitive layer which produces an interface voltage that changes due to the ion, and a transistor that has a gate electrode coupled to the ion sensitive layer, a source terminal, and a drain terminal, the source terminal being configured to output electric signals caused by a variation in the interface voltage,
wherein a switching device is connected to the gate electrode of the transistor and configured to turn a connection between a voltage source and the gate electrode of the transistor ON and OFF,
wherein a reading circuit is connected to the transistor, and includes a current source configured to keep a drain current of the transistor constant and a circuit configured to keep a source-drain voltage of the transistor constant,
wherein the reading circuit is configured to extract a variation in a threshold voltage of the transistor from a variation in a source voltage of the source terminal, and output the variation in the threshold voltage,
wherein the controller is further programmed to control the switching device, the solution sender and the trigger generator so that the solution sender starts transmitting the reagent onto the biomolecule sample disposed on the semiconductor sensor, the switching device turns ON the connection between the gate electrode of the transistor and the voltage source, the switching device turns OFF the connection between the gate electrode of the transistor and the voltage source, and thereafter the trigger generator generates the physical environment, and
wherein the processor is further programmed to identify a configuration of the biomolecule sample according to a measured result corresponding to the variation in the threshold voltage of the transistor in a period after the trigger generator generates the physical environment to identify the configuration of the biomolecule sample.

11. The biomolecule measuring device according to claim 10, further comprising:
a reagent remover that transmits a medium onto the semiconductor sensor to remove the reagent therefrom,
wherein the semiconductor sensor includes a concave portion that receives the biomolecule sample and the reagent,
wherein the ion sensitive layer is connected to a bottom of the concave portion, and
wherein the controller is configured to control the reagent remover to transmit the medium to remove the reagent that is present outside of the concave portion and thereafter control the switching device to turn OFF the connection between the voltage source and the gate electrode of the transistor.

12. The biomolecule measuring device according to claim 11,
wherein the semiconductor sensor includes a substrate on which the concave portion is formed, and
wherein a surface of the substrate is coated with a water-repellent material.

13. The biomolecule measuring device according to claim 10, further comprising:
a reagent remover that transmits a medium onto the semiconductor sensor to remove the reagent therefrom,
wherein the semiconductor sensor includes a concave portion that receives the biomolecule sample and the reagent,
wherein the controller is configured to control the reagent remover to transmit the medium to remove the reagent that is present outside of the concave portion, and
wherein the controller is configured to control the switching device to turn OFF the connection between the voltage source and the gate electrode of the transistor after the reagent remover removes the reagent that is present outside of the concave portion, and thereafter cause the trigger generator to generate the physical environment.

14. The biomolecule measuring device according to claim 10,
wherein the voltage source is fixed at ground voltage.

* * * * *